United States Patent [19]

Armour et al.

[11] Patent Number: 5,703,240
[45] Date of Patent: Dec. 30, 1997

[54] PIPERIDINE DERIVATIVES

[75] Inventors: Duncan Robert Armour; Brian Evans; David Middlemiss; Alan Naylor; Neil Anthony Pegg; Maria Victoria Vinader; Gerard Martin Paul Giblin, all of Stevenage; Tania Hubbard, Fulbourn; Michael Menteith Hann, Stevenage; Xiao-Qing Lewell, Stevenage; Stephen Paul Watson, Stevenage, all of Great Britain

[73] Assignee: Glaxo Group Limited, London, England

[21] Appl. No.: 612,843

[22] PCT Filed: Sep. 20, 1994

[86] PCT No.: PCT/EP94/03129

§ 371 Date: Mar. 21, 1996

§ 102(e) Date: Mar. 21, 1996

[87] PCT Pub. No.: WO95/08549

PCT Pub. Date: Mar. 30, 1995

[30] Foreign Application Priority Data

Sep. 22, 1993 [GB] United Kingdom ............ 9319606
Dec. 31, 1993 [GB] United Kingdom ............ 9326583

[51] Int. Cl.$^6$ ............... C07D 401/10; A61K 31/445
[52] U.S. Cl. ............................... 546/210; 514/326
[58] Field of Search ............ 546/210; 514/326, 514/299

[56] References Cited

U.S. PATENT DOCUMENTS

| 5,232,929 | 8/1993 | Desai et al. ............ 514/314 |
| 5,332,817 | 7/1994 | Desai et al. ............ 546/16 |

FOREIGN PATENT DOCUMENTS

| 0 436 334 | 7/1991 | European Pat. Off. |
| WO-A-93 00331 | 1/1993 | WIPO |
| WO-A-93 01170 | 1/1993 | WIPO |
| WO 94/13663 | 6/1994 | WIPO |

OTHER PUBLICATIONS

Maggi, C.A. et al.: Tachykinin Receptors and tachykinin receptor antagonists. J. Auton. Pharmacal. (1993) vol. 13, pp. 60-66.

Primary Examiner—C. Warren Ivy
Assistant Examiner—Charanjit S. Awlakm
Attorney, Agent, or Firm—Bacon & Thomas

[57] ABSTRACT

The present invention relates to piperidine derivatives of formula (I)

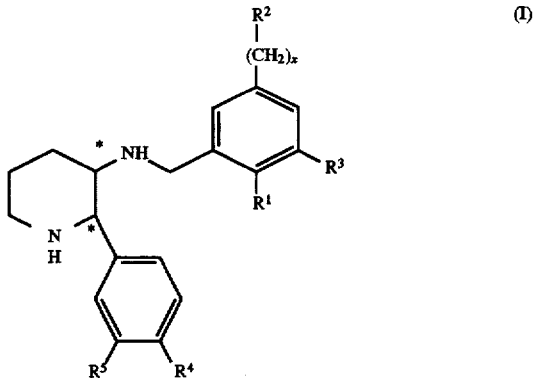

wherein $R^1$ is a $C_{1-4}$alkoxy group;

$R^2$ is

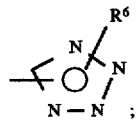

$R^3$ is a hydrogen or halogen atom;

$R^4$ and $R^5$ may each independently represent a hydrogen or halogen atom, or a $C_{1-4}$alkyl, $C_{1-4}$alkoxy or trifluoromethyl group;

$R^6$ is a hydrogen atom, a $C_{1-4}$alkyl, $(CH_2)_m$cyclopropyl, $-S(O)_n C_{1-4}$alkyl, phenyl, $NR^7R^8$, $CH_2C(O)CF_3$ or trifluoromethyl group;

$R^7$ and $R^8$ may each independently represent a hydrogen atom, or a $C_{1-4}$alkyl or acyl group;

x represents zero or 1;

n represents zero, 1 or 2;

m represents zero or 1;

and pharmaceutically acceptable salts and solvates thereof; to processes for their preparation; and their use in the treatment of conditions mediated by tachykinins.

20 Claims, No Drawings

PIPERIDINE DERIVATIVES

The present invention relates to piperidine derivatives, to process for their preparation, pharmaceutical compositions containing them and their medical use.

In particular the invention relates to novel compounds which are potent and specific antagonists of tachykinins, including substance P and other neurokinins.

3-Aminopiperidine derivatives described as having substance P antagonist activity are disclosed in, for example, PCT Patent Applications WO-A-9109844 and WO-A-9301170.

The present invention provides compounds of formula (I)

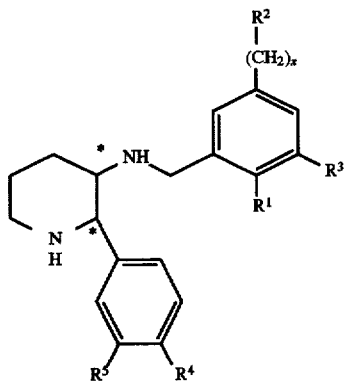

wherein $R^1$ is a $C_{1-4}$alkoxy group;
$R^2$ is

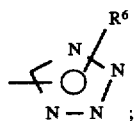

$R^3$ is a hydrogen or halogen atom;

$R^4$ and $R^5$ may each independently represent a hydrogen or halogen atom, or a $C_{1-4}$alkyl, $C_{1-4}$alkoxy or trifluoromethyl group;

$R^6$ is a hydrogen atom, a $C_{1-4}$alkyl, $(CH_2)_m$cyclopropyl, $-S(O)_nC_{1-4}$alkyl, phenyl, $NR^7R^8$, $CH_2C(O)CF_3$ or trifluoromethyl group;

$R^7$ and $R^8$ may each independently represent a hydrogen atom, or a $C_{1-4}$alkyl or acyl group;

x represents zero or 1;

n represents zero, 1 or 2;

m represents zero or 1;

and pharmaceutically acceptable salts and solvates thereof.

Suitable pharmaceutically acceptable salts of the compounds of general formula (I) include acid addition salts formed with pharmaceutically acceptable organic or inorganic acids for example, hydrochlorides, hydrobromides, sulphates, alkyl- or arylsulphonates (e.g. methanesulphonates or p-toluenesulphonates), phosphates, acetates, citrates, succinates, tartrates, fumarates and maleates. Dihydrochloride salts are particularly suitable.

Other acids, such as oxalic, while not in themselves pharmaceutically acceptable, may be useful in the preparation of salts useful as intermediates in obtaining the compounds of formula (I) and their pharmaceutically acceptable acid addition salts.

The solvates may, for example, be hydrates.

References hereinafter to a compound according to the invention includes both compounds of formula (I) and their pharmaceutically acceptable acid addition salts together with pharmaceutically acceptable solvates.

It will be appreciated by those skilled in the art that the compounds of formula (I) contain at least two chiral centres (shown as * in formula (I)) and thus exist in the form of two pairs of optical isomers (i.e. enantiomers) and mixtures thereof including racemic mixtures.

For example the compounds of formula (I) may be either cis isomers, as represented by figures (a) and (b), or trans isomers, as represented by figures (c) and (d), or mixtures thereof.

All of the isomers of the compounds of formula (I) represented by the figures (a) to (d) and mixtures thereof including racemic mixtures are included within the scope of the invention.

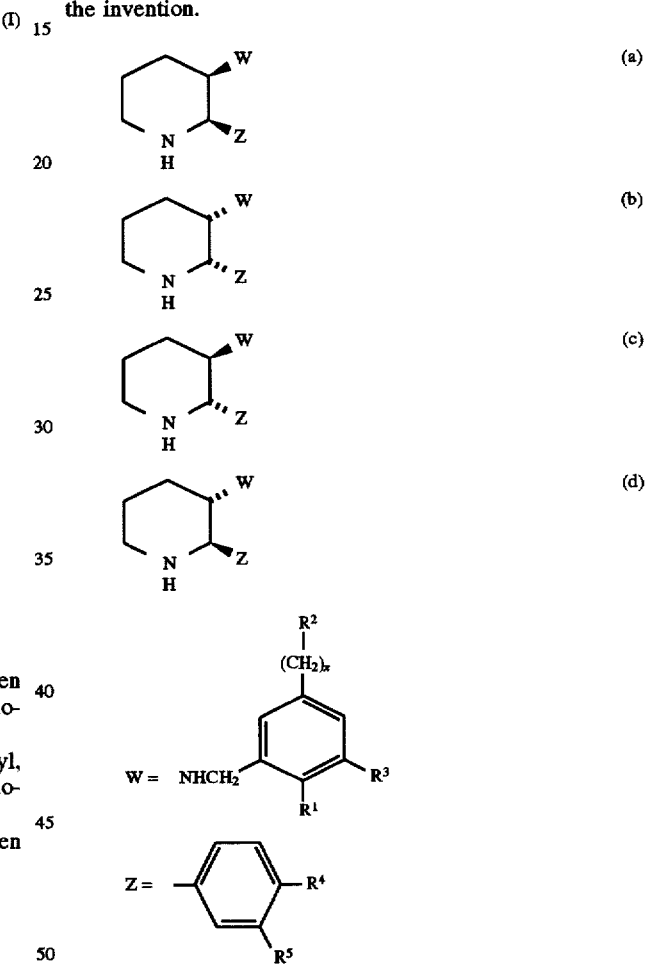

The compounds of formula (I) are preferably in the form of their cis isomers (i.e. as represented by figures (a) and (b)). The 2S,3S isomers (i.e. as represented by figure (b)) are particularly preferred.

Referring to the general formula (I), a $C_{1-4}$alkoxy group may be a straight chain or branched chain alkoxy group, for example, methoxy, ethoxy, propoxy, prop-2-oxy, butoxy, but-2-oxy or 2-methylprop-2-oxy. A $C_{1-4}$alkyl group may be a straight chain or branched chain alkyl group and may be, for example, methyl, ethyl, propyl, prop-2-yl, butyl, but-2-yl, 2-methylprop-1-yl or 2-methylprop-2-yl.

Referring to the general formula (I), a halogen atom may be a fluorine, chlorine, bromine or iodine atom, such as a fluorine, chlorine or bromine atom.

Referring to the general formula (I), $R^1$ is suitably a methoxy, ethoxy or prop-2-oxy group.

Referring to the general formula (I), R² is suitably a group

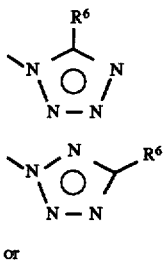

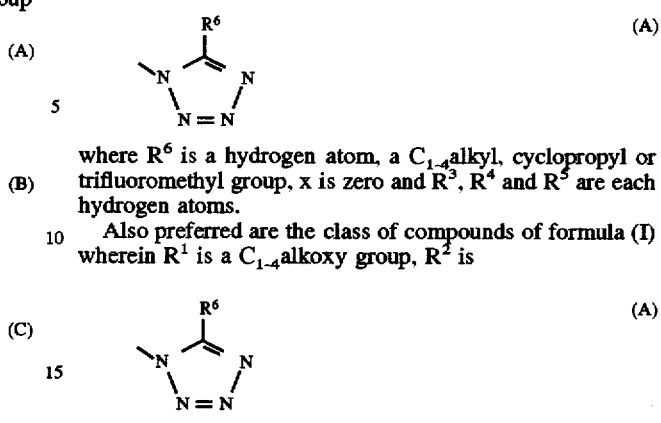

where R⁶ is a hydrogen atom, a $C_{1-4}$alkyl, cyclopropyl or trifluoromethyl group, x is zero and R³, R⁴ and R⁵ are each hydrogen atoms.

Also preferred are the class of compounds of formula (I) wherein R¹ is a $C_{1-4}$alkoxy group, R² is

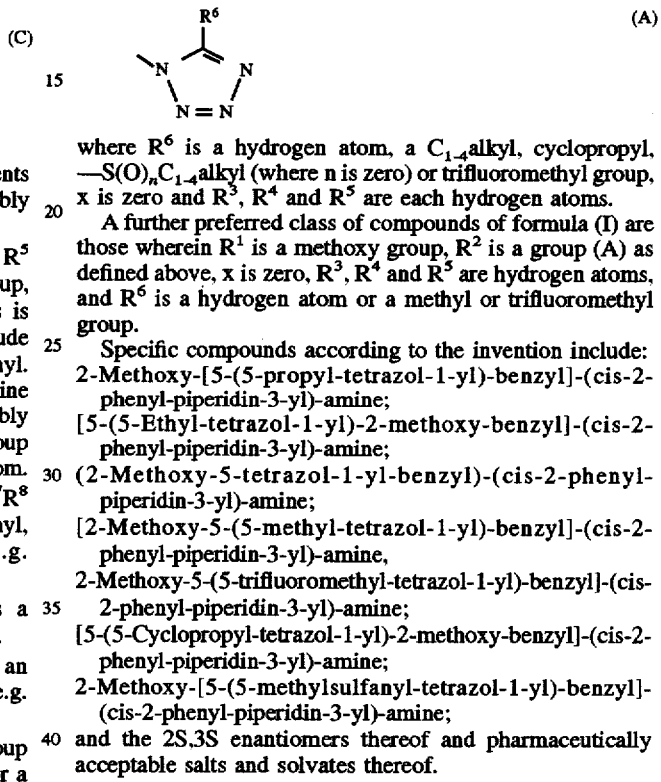

where R⁶ is a hydrogen atom, a $C_{1-4}$alkyl, cyclopropyl, —S(O)$_n$C$_{1-4}$alkyl (where n is zero) or trifluoromethyl group, x is zero and R³, R⁴ and R⁵ are each hydrogen atoms.

A further preferred class of compounds of formula (I) are those wherein R¹ is a methoxy group, R² is a group (A) as defined above, x is zero, R³, R⁴ and R⁵ are hydrogen atoms, and R⁶ is a hydrogen atom or a methyl or trifluoromethyl group.

Specific compounds according to the invention include:
2-Methoxy-[5-(5-propyl-tetrazol-1-yl)-benzyl]-(cis-2-phenyl-piperidin-3-yl)-amine;
[5-(5-Ethyl-tetrazol-1-yl)-2-methoxy-benzyl]-(cis-2-phenyl-piperidin-3-yl)-amine;
(2-Methoxy-5-tetrazol-1-yl-benzyl)-(cis-2-phenyl-piperidin-3-yl)-amine;
[2-Methoxy-5-(5-methyl-tetrazol-1-yl)-benzyl]-(cis-2-phenyl-piperidin-3-yl)-amine;
2-Methoxy-5-(5-trifluoromethyl-tetrazol-1-yl)-benzyl]-(cis-2-phenyl-piperidin-3-yl)-amine;
[5-(5-Cyclopropyl-tetrazol-1-yl)-2-methoxy-benzyl]-(cis-2-phenyl-piperidin-3-yl)-amine;
2-Methoxy-[5-(5-methylsulfanyl-tetrazol-1-yl)-benzyl]-(cis-2-phenyl-piperidin-3-yl)-amine;
and the 2S,3S enantiomers thereof and pharmaceutically acceptable salts and solvates thereof.

Additional compounds according to the invention include:
cis-(2-Methoxy-5-tetrazol-1-yl-benzyl)-(2-p-tolyl-piperidin-3-yl)-amine;
cis-[2-Methoxy-5-(5-trifluoromethyl-tetrazol-1-yl)-benzyl]-[2-p-tolyl-piperidin-3-yl]-amine;
cis-[2-Methoxy-5-(5-methyl-tetrazol-1-yl)-benzyl]-(2-p-tolyl-piperidin-3-yl)-amine;
cis-[2-(3-Bromo-phenyl)-piperidin-3-yl]-(2-methoxy-5-tetrazol-1-yl-benzyl)-amine;
cis-[2-Methoxy-5-(5-methyl-tetrazol-1-yl)-benzyl]-[2-(4-methoxy-phenyl)-piperidin-3-yl]-amine;
cis-[2-(3-Bromo-4-methyl-phenyl)-piperidin-3-]-[2-methoxy-5-(5-methyl-tetrazol-1-yl)-benzyl]-amine;
cis-[2-(3-Chloro-phenyl)-piperidin-3-yl]-(2-methoxy-5-tetrazol-1-yl-benzyl)-amine;
cis-[2-(3-Fluoro-phenyl)-piperidin-3-yl]-[2-methoxy-5-(5-trifluoromethyl-tetrazol-1-yl)-benzyl]-amine;
cis-[2-(3-Fluoro-4-methylphenyl)-piperidin-3-yl-[2-methoxy-5-(5-methyltetrazol-1-yl)-benzyl]-amine;
cis-[2-(3-Fluorophenyl)-piperidin-3-yl]-[2-methoxy-5-(5-methyltetrazol-1-yl)-benzyl]-amine;
cis-2-(4-Fluorophenyl)-piperidin-3-yl]-[2-methoxy-5-(methyltetrazol-1-yl)-benzyl]-amine;
cis-[2-(3,4-Difluorophenyl)-piperidin-3-yl]-[2-methoxy-5-(5-methyltetrazol-1-yl)-benzyl]-amine;

Referring to the general formula (I), when R³ represents a halogen atom, this is suitably chlorine, or more preferably fluorine.

Referring to the general formula (I), when R⁴ or R⁵ represents a $C_{1-4}$alkyl group this is suitably a methyl group, or when R⁴ or R⁵ represents a $C_{1-4}$alkoxy group this is suitably a methoxy group. Suitable values for R⁴ include hydrogen, methyl, methoxy, fluorine or trifluoromethyl. Suitable values for R⁵ include hydrogen, fluorine, chlorine or bromine. R⁴ and R⁵ are suitably both hydrogen or suitably both fluorine or suitably one of R⁴ and R⁵ is a methyl group and the other is a halogen, e.g. a fluorine or bromine, atom.

Referring to the general formula (I), when R⁶ is an NR⁷R⁸ group, this is suitably NH₂, NH($C_{1-4}$alkyl) e.g. NHmethyl, NHacyl i.e. NHC(O)methyl, or N($C_{1-4}$alkyl)₂ e.g. N(methyl)₂ or N(ethyl)₂.

Referring to the general formula (I), when R⁶ is a $C_{1-4}$alkyl group, this is suitably methyl, ethyl or propyl.

Referring to the general formula (I), when R⁶ is an —S(O)$_n$C$_{1-4}$alkyl group, this is suitably —S(O)$_n$methyl, e.g. —S-methyl or —SO₂methyl.

Referring to the general formula (I), when R² is a group (A) as defined above, R⁶ is suitably a hydrogen atom or a $C_{1-4}$alkyl, e.g. methyl, ethyl or propyl, (CH₂)$_m$cyclopropyl, where m is zero, S(O)$_n$C$_{1-4}$alkyl, e.g. —S(O)$_n$methyl such as —S-methyl or —SO₂methyl, phenyl, NR⁷R⁸, e.g. NH₂, NH($C_{1-4}$alkyl) e.g. NHmethyl, NHacyl i.e. NHC(O)methyl, or N($C_{1-4}$alkyl)₂ e.g. N(methyl)₂ or N(ethyl)₂, CH₂C(O)CF₃ or a trifluoromethyl group.

Referring to the general formula (I), when R² is a group (B) as defined above, R⁶ is suitably hydrogen. When R² is a group (C) as defined above, R⁶ is suitably a $C_{1-4}$alkyl, e.g. methyl or ethyl, or a (CH₂)$_m$cyclopropyl, where m is 1, group.

Referring to the general formula (I), when R² is a group (A) as defined above, x is suitably zero or 1. When R² is a group (B) as defined above, x is suitably zero or 1. When R² is a group (C) as defined above, x is suitably zero.

R¹ is preferably a methoxy group.
R² is preferably a group (A) as defined above.
R³ is preferably a hydrogen atom.
R⁴ and R⁵ are preferably hydrogen atoms.
R⁶ is preferably a hydrogen atom, a $C_{1-4}$alkyl, e.g. methyl, or a trifluoromethyl group.
x Is preferably zero.

A preferred class of compounds of formula (I) are those wherein R¹ is a $C_{1-4}$alkoxy group, R² is cis-[2-(3,4-Difluorophenyl)-piperidin-3-yl]-[2-methoxy-5-tetrazol-1-yl-benzyl]-amine;

cis-[2-(3,4-Difluoro-phenyl)-piperidin-3-yl]-[2-methoxy-5-(5-trifluoromethyl-tetrazol-1-yl)-benzyl]-amine;

cis-[2-Methoxy-5-(5-methyl-tetrazol-1-yl)-benzyl]-[2-(4-trifluoromethyl-phenyl)-piperidin-3-yl]-amine;

cis-(2-Methoxy-5-tetrazol-1-yl-benzyl)-[2-(4-trifluoromethyl-phenyl)-piperidin-3-yl]-amine;

especially the 2S,3S enantiomers thereof and:

[2-Methoxy-5-(5-phenyl-tetrazol-1-yl)-benzyl]-(2S-phenyl-piperidin-3S-yl)-amine;

[2-Methoxy-5-(5-methylimino-4,5-dihydro-tetrazol-1-yl)-benzyl]-(2S-phenylpiperidin-3S-yl)-amine;

N-(1-{4-Methoxy-3-[(2S-phenyl-piperidin-3S-ylamino)-methyl]-phenyl}-1H-tetrazol-5-yl)-acetamide;

[5-(5-Dimethylamino-tetrazol-1-yl)-2-methoxy-benzyl]-(2S-phenyl-piperidin-3S-yl)-amine;

[5-(5-Diethylamino-tetrazol-1-yl)-2-methoxy-benzyl]-(2S-phenyl-piperidin-3S-yl)-amine;

1,1,1-Trifluoro-3-(1-{4-methoxy-3-[(2S-phenyl-piperidin-3S-ylamino)-methyl]-phenyl}-1H-tetrazol-5-yl)-propan-2-one;

[5-(5-Methanesulfonyl-tetrazol-1-yl)-2-methoxy-benzyl]-(2S-phenyl-piperidin-3S-yl)-amine;

[3-Chloro-2-methoxy-5-(5-methyl-tetrazol-1-yl)-benzyl]-(2S-phenyl-piperidin-3S-yl)-amine;

[2S-(4-Fluoro-phenyl)-piperidin-3S-yl]-[2-methoxy-5-(5-trifluoromethyl-tetrazol-1-yl)-benzyl]-amine;

(2S,3S)-[2-(4-Fluorophenyl)-piperidin-3-yl]-(2-methoxy-5-tetrazol-1-yl-benzyl)-amine;

(5-(5-Amino-tetrazol-1-yl)-2-methoxy-benzyl]-(2S-phenyl-piperidin-3S-yl)-amine;

(2-Ethoxy-5-tetrazol-1-yl-benzyl)-([2S,3S]-2-phenyl piperidin-3-yl) amine; (2-isopropoxy-5-tetrazol-1-ylbenzyl)-[(2S,3S]-2-phenyl piperidin-3-yl) amine;

and pharmaceutically acceptable salts and solvates thereof.

Preferred compounds according to the invention are:
(2-Methoxy-5-tetrazol-1-yl-benzyl)-(2S-phenyl-piperidin-3S-yl)-amine; and
[2-Methoxy-5-(5-trifluoromethyl-tetrazol-1-yl)-benzyl]-(2S-phenyl-piperidin-3S-yl)-amine;

and pharmaceutically acceptable salts, especially the dihydrochloride salts, and solvates thereof.

It will be appreciated that chemical compounds can be named in different ways and according to different naming conventions. For example "(2-Methoxy-5-tetrazol-1-yl-benzyl)-([2S,3S]-2-phenyl-piperidin-3-yl)-amine dihydrochloride" may also be named as "[(2-Methoxy-5-tetrazol-1-yl-benzyl)-([2S,3S]-2-phenyl-piperidin-3-yl)-amine [2S]-phenyl-piperidin-[3S]-ylamine dihydrochloride]" or "(2-Methoxy-5-tetrazol-1-yl-benzyl)-(2S-phenyl-piperidin-3S-yl)-amine dihydrochloride". "(2-Methoxy-5-tetrazol-1-yl-benzyl)-(cis-2-phenyl-piperidin-3-yl)-amine" may also be named as "cis-(2-Methoxy-5-tetrazol-1-yl-benzyl)-(2-phenyl-piperidin-3-yl)-amine". Compounds may be name ". . . -3-piperidinamine" or ". . . piperidin-3-ylamine". All names are equally correct. Note that the R, S notation may appear within square brackets (e.g. [2S]) or without square brackets.

The compounds of the invention are antagonists of tachykinins, including substance P and other neurokinins both in vitro and in vivo and are thus of use in the treatment of conditions mediated by tachykinins, including substance P and other neurokinins.

The compounds of the invention possess $NK_1$-receptor binding affinity as determined in vitro by their ability to displace [3H]-substance P (SP) from $NK_1$ receptors in cell membranes of U-373MG human astrocytoma cells. U-373MG membranes (25–35 μg protein per tube) were prepared and incubated with [3H]-SP (0.6–0.8 nM) at 20° C. for 40 min. Non-specific binding was defined as that remaining in the presence of 1 μM (+) CP-99,994.

$NK_1$-receptor binding affinity has also been determined in vitro by the compounds' ability to displace [3H]-substance P (SP) from recombinant human $NK_1$ receptors expressed in Chinese Hamster Ovary (CHO) cell membranes. CHO membranes (3–5 μg protein per tube) were prepared and incubated with [3]-SP (0.6–0.8 nM) at 20° C. for 40 min. Non-specific binding was defined as that remaining in the presence of 1 μM (+) CP99,994.

The compounds of the invention have been shown to have anti-emetic activity as indicated by for example their ability to inhibit radiation-induced emesis in the ferret. In this model of emesis the onset of retching and vomiting occurs approximately 20 minutes after whole body irradiation (2 Grey=200 Rads). The test compound is administered (e.g. i.p, p.o., i.v., s.c) immediately after irradiation and its effect on emesis determined by comparison with appropriate controls.

Anti-emetic activity may also be demonstrated using other emetogens such as cisplatin and ipecacuanha. Alternatively, the test compounds may be administered before irradiation or before treatment with an emetogen, for example 1.5, 3 or 6 hours before irradiation.

Compounds of the invention have been shown to inhibit radiation-induced emesis at a dose of 0.03–3 mg/kg s.c. in the above test.

The compounds of the invention are potent and specific $NK_1$ antagonists. Furthermore, they exhibit good oral bioavailability and have an advantageous duration of action.

Compounds of the invention are useful as analgesics in particular they are useful in the treatment of traumatic pain such as postoperative pain; traumatic avulsion pain such as brachial plexus; chronic pain such as arthritic pain such as occurring in osteo-, rheumatoid or psoriatic arthritis; neuropathic pain such as post-herpetic neuralgia, trigeminal neuralgia, segmental or intercostal neuralgia, fibromyalgia, causalgia, peripheral neuropathy, diabetic neuropathy, chemotherapy-induced neuropathy, AIDS related neuropathy, occipital neuralgia, geniculate neuralgia, glossopharyngeal neuralgia, reflex sympathetic dystrophy, phantom limb pain; various forms of headache such as migraine, acute or chronic tension headache, temporomandibular pain, maxillary sinus pain, cluster headache; odontalgia; cancer pain; pain of visceral origin; gastrointestinal pain; nerve entrapment pain; sport's injury pain; dysmennorrhoea; menstrual pain; meningitis; arachnoiditis; musculoskeletal pain; low back pain e.g. spinal stenosis; prolapsed disc; sciatica; angina; ankylosing spondyolitis; gout; burns; scar pain; itch; and thalamic pain such as post stroke thalamic pain.

Compounds of the invention are also useful as antiinflammatory agents in particular they are useful in the treatment of inflammation in asthma, influenza, chronic bronchitis and rheumatoid arthritis; in the treatment of inflammatory diseases of the gastrointestinal tract such as Crohn's disease, ulcerative colitis, inflammatory bowel disease and non-steroidal anti-inflammatory drug induced damage; inflammatory diseases of the skin such as herpes and eczema; inflammatory diseases of the bladder such as cystitis and urge (i.e., urinary) incontinence; and eye and dental inflammation.

Compounds of the invention am also useful in the treatment of allergic disorders in particular allergic disorders of the skin such as urticaria, and allergic disorders of the airways such as rhinitis.

Compounds of the invention may also be useful in the treatment of CNS disorders in particular psychoses such as schizophrenia, mania or dementia; cognitive disorders e.g. Alzheimer's disease; anxiety; AIDS related dementia; diabetic neuropathy; multiple sclerosis; depression; Parkinson's disease; and dependency on drugs or substances of abuse; and also the compounds of the invention may act as myorelaxants and antispasmodics.

Compounds of the invention are also useful in the treatment of emesis, i.e. nausea, retching and vomiting. Emesis includes acute emesis, delayed or late emesis and anticipatory emesis. The compounds of the invention, are useful in the treatment of emesis however induced. For example, emesis may be induced by drugs such as cancer chemotherapeutic agents such as alkylating agents, e.g. cyclophosphamide, carmustine, lomustine and chlorambucil; cytotoxic antibiotics, e.g. dactinomycin, doxorubicin, mitomycin-C and bleomycin; anti-metabolites, e.g. cytarabine, methotrexate and 5-fluorouracil; vinca alkaloids, e.g. etoposide, vinblastine and vincristine; and others such as cisplatin, dacarbazine, procarbazine and hydroxyurea; and combinations thereof; radiation sickness; radiation therapy, e.g. irradiation of the thorax or abdomen, such as in the treatment of cancer; poisons; toxins such as toxins caused by metabolic disorders or by infection, e.g. gastritis, or released during bacterial or viral gastrointestinal infection; pregnancy; vestibular disorders, such as motion sickness, vertigo, dizziness and Meniere's disease; post-operative sickness; gastrointestinal obstruction; reduced gastrointestinal motility; visceral pain, e.g. myocardial infarction or peritonitis; migraine; increased intercranial pressure; decreased intercranial pressure (e.g. altitude sickness); opioid analgesics, such as morphine; and gastro-oesophageal reflux disease, acid indigestion, over-indulgence of food or drink, acid stomach, sour stomach, waterbrash/regurgitation, heartburn, such as episodic heartburn, nocturnal heartburn, and meal-induced heartburn and dyspepsia.

Compounds of the invention are also useful in the treatment of gastrointegstinal disorders such as irritable bowel syndrome; skin disorders such as psoriasis, pruritis and sunburn; vasospastic diseases such as angina, vascular headache and Reynaud's disease; cerebral ischeamia such as cerebral vasospasm following subarachnoid haemorrhage; fibrosing and collagen diseases such as scleroderma and eosinophilic fascioliasis; disorders related to immune enhancement or suppression such as systemic lupus erythematosus and rheumatic diseases such as fibrositis; and cough.

The invention therefore provides a compound of formula (I) or a pharmaceutically acceptable salt or solvate thereof for use in therapy, in particular in human medicine.

There is also provided as a further aspect of the invention the use of a compound of formula (I) or a pharmaceutically acceptable salt or solvate thereof in the preparation of a medicament for use in the treatment of conditions mediated by tachykinins, including substance P and other neurokinins.

In an alternative or further aspect there is provided a method for the treatment of a mammal, including man, in particular in the treatment of conditions mediated by tachykinins, including substance P and other neurokinins, comprising administration of an effective amount of a compound of formula (I) or a pharmaceutically acceptable salt thereof.

It will be appreciated that reference to treatment is intended to include prophylaxis as well as the alleviation of established symptoms. Compounds of formula (I) may be administered as the raw chemical but the active ingredient is preferably presented as a pharmaceutical formulation.

Accordingly, the invention also provides a pharmaceutical composition which comprises at least one compound of formula (I) or a pharmaceutically acceptable salt thereof and formulated for administration by any convenient route. Such compositions are preferably in a form adapted for use in medicine, in particular human medicine, and can conveniently be formulated in a conventional manner using one or more pharmaceutically acceptable carriers or excipients.

Thus compounds of formula (I) may be formulated for oral, buccal, paranteral, topical (including ophthalmic and nasal), depot or rectal administration or in a form suitable for administration by inhalation or insufflation (either through the mouth or nose).

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavouring, colouring and sweetening agents as appropriate.

Preparations for oral administration may be suitably formulated to give controlled release of the active compound.

For buccal administration the composition may take the form of tablets or lozenges formulated in conventional manner.

The compounds of the invention may be formulated for parenteral administration by bolus injection or continuous infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use.

The compounds of the invention may be formulated for topical administration in the form of ointments, creams, gels, lotions, pessaries, aerosols or drops (e.g. eye, ear or nose drops). Ointments and creams may, for example, be formulated with an aqueous or oily base with the addition of suitable thickening and/or gelling agents. Ointments for administration to the eye may be manufactured in a sterile manner using sterilised components.

Lotions may be formulated with an aqueous or oily base and will in general also contain one or more emulsifying agents, stabilising agents, dispersing agents, suspending agents, thickening agents, or colouring agents. Drops may be formulated with an aqueous or non aqueous base also comprising one or more dispersing agents, stabilising agents, solubilising agents or suspending agents. They may also contain a preservative.

The compounds of the invention may also be formulated in rectal compositions such as suppositories or retention enemas, e.g. containing conventional suppository bases such as cocoa butter or other glycerides.

The compounds of the invention may also be formulated as depot preparations. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

For intranasal administration, the compounds of the invention may be formulated as solutions for administration via a suitable metered or unit dose device or alternatively as a powder mix with a suitable carrier for administration using a suitable delivery device.

The compositions may contain from 0.1% upwards, e.g. 0.1–99% of the active material, depending on the method of administration. A proposed dose of the compounds of the invention is 0.05 mg/kg to about 400 mg/kg bodyweight per day e.g. 0.05 mg/kg to 5 mg/kg per day. It will be appreciated that it may be necessary to make routine variations to the dosage, depending on the age and condition of the patient and the precise dosage will be ultimately at the discretion of the attendant physician or veterinarian. The dosage will also depend on the route of administration and the particular compound selected.

The compounds of formula (I) may, if desired, be administered with one or more therapeutic agents and formulated for administration by any convenient route in a conventional manner. Appropriate doses will be readily appreciated by those skilled in the art. For example, the compounds of formula (I) may be administered in combination with a systematic anti-inflammatory corticosteroid such as methyl prednisolone or dexamethasone, or a 5HT$_3$ antagonist such as ondansetron, granisetron or metoclopramide. Antagonists of tachykinins, including substance P and other neurokinins, for example, the compounds of formula (I), may also be administered in combination with sympathomimetics such as ephedrine, pseudoephedrine and oxymetazoline. Compounds which are specific antagonists at NK$_1$ receptors, such as the compounds of formula (I), may be administered in combination with compounds which are specific antagonists at NK$_2$ receptors.

Compounds of formula (I), and salts and solvates thereof, may be prepared by the general methods outlined hereinafter. In the following description, the groups $R^1$, $R^2$, $R^3$, $R^4$ and $R^5$ and x are as previously defined for compounds of formula (I) unless otherwise stated.

According to a first general process (A), a compound of formula (I) may be prepared by reacting a compound of formula (II):

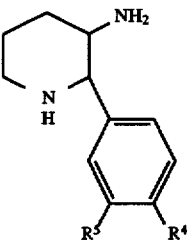

with a compound of formula (III)

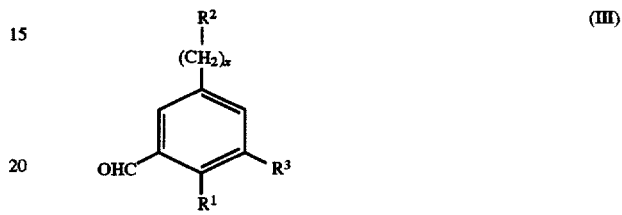

to form the intermediate imine, which may be isolated if required, followed by reduction of the imine using a suitable metal reducing agent such as a metal hydride, for example a borane hydride, alane hydride or a metal hydride complex like lithium aluminum hydride or sodium borohydride, or an organo-metallic complex such as borane- methyl sulphide, 9-borabicyclononane (9-BBN), triethylsilane, sodium triacetoxyborohydride, sodium cyanoborohydride and the like. Alternatively, catalytic hydrogenation may be used, for example using a platinum catalyst in a suitable solvent e.g. ethanol.

The condensation reaction conveniently takes place in a suitable solvent such as an alcohol (e.g. methanol), an aromatic hydrocarbon (e.g. benzene, toluene or xylene) or a chlorinated hydrocarbon (e,g. dichloromethane or dichloroethane) at a temperature ranging from ambient to the reflux temperature of the reaction mixture. The reaction preferably takes place in the presence of a catalytic amount of a suitable acidic condensing agent such as p-toluenesulphonic acid or acetic acid and/or a dehydrating agent such as molecular sieves, or the reaction may take place under Dean-Stark conditions.

The reduction step conveniently takes place in a suitable solvent such as acetonitrile, dimethylformamide, benzene, chlorinated hydrocarbons such as dichloromethane or dichloroethane, ethers such as diethyl ether, tetrahydrofuran, dioxane and 1,2-dimethoxyethane and alcohols such as ethanol at a temperature ranging from 0° C. to the reflux temperature of the reaction mixture.

Process (A) may also take place in one step without isolation of the intermediate imine if the condensation reaction takes place in the presence of sodium cyanoborohydride or sodium triacetoxyborohydride. Further reduction is therefore unnecessary in this case.

When carrying out process (A) where $R^2$ is a group (C) as defined hereinbefore, $R^6$ is preferably a $C_{1-4}$alkyl group.

Compounds of formula (II) may be prepared by reducing compounds of formula (IV)

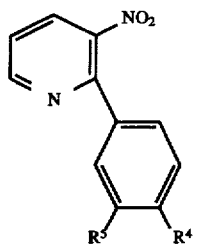

under suitable reducing conditions, such as catalytic hydrogenation, for example using a platinum catalyst, e.g. platinum (IV) oxide, in a suitable solvent like ethanol, preferably in the presence of concentrated hydrochloric acid.

Compounds of formula (IV) may be prepared by reacting 2-chloro-3-nitropyridine with a compound of formula (V)

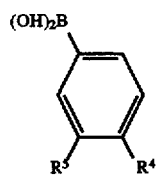

in the presence of a palladium (O) catalyst such as tetrakis (triphenyl phosphine) palladium (O). The reaction suitably takes place in the presence of a solvent such as an ether, e.g. dimethoxyethane, at an elevated temperature and preferably in the presence of a base such as sodium carbonate.

Compounds of formula (V) may be prepared by reacting the corresponding bromo-compounds under Grignard conditions followed by reaction with tri-isopropylborate, Alternatively, compounds of formula (II) may be prepared by reducing compounds of formula (VI)

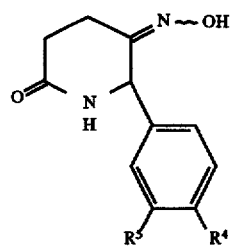

under suitable reducing conditions, for example using a metal hydride complex such as sodium borohydride in the presence of zirconium (IV) chloride in a suitable solvent such as tetrahydrofuran.

Compounds of formula (VI) may be prepared by reacting compounds of formula (VII)

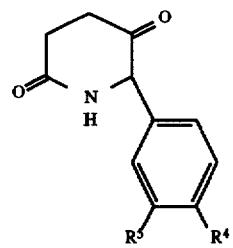

with hydroxylamine hydrochloride in the presence of pyridine.

Compounds of formula (VII) may be prepared by reading compounds of formula (VIII)

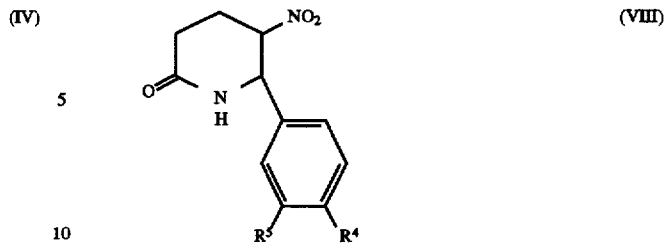

with ozone in the presence of potassium t-butoxide in a suitable solvent such as a mixture of dichloromethane and methanol.

Compounds of formula (VIII) may be prepared by reading compounds of formula (IX)

with methyl-4-nitrobutyrate and ammonium acetate, in a suitable solvent such as an alcohol, e.g. ethanol at elevated temperature.

Compounds of formula (III) may be prepared by reading compounds of formula (X)

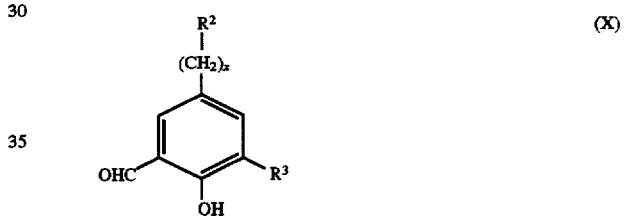

with a $C_{1-4}$alkylating agent, such as a $C_{1-4}$alkyl iodide, in the presence of a base such as potassium carbonate.

Compounds of formula (X) may be prepared by reacting compounds of formula (XI)

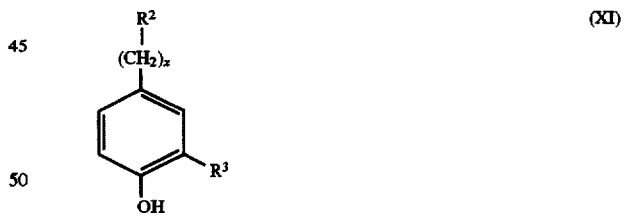

with hexamethylenetetramine in the presence of trifluoroacetic acid at elevated temperature.

Compounds of formula (XI) where $R^2$ is a group (A) as defined hereinbefore and x is zero may be prepared by reacting the appropriate p-hydroxyaniline, or a protected derivative thereof, with compounds of formula (XII)

(where $R^9$ is methyl or ethyl), for example triethylorthoacetate, in acetic acid followed by reaction with sodium azide at elevated temperature and deprotection if necessary.

Compounds of formula (XI) where $R^2$ is a group (A) as defined hereinbefore and x is zero may also be prepared by reacting a compound of formula (XIII)

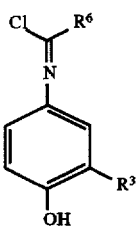 (XIII)

or a protected derivative thereof, with sodium azide in acetic acid at elevated temperature, followed by deprotection if necessary.

Compounds of formula (XIII) may be prepared by reacting a compound of formula (XIV)

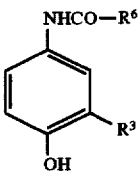 (XIV)

or a protected derivative thereof, with resin-supported triphenylphosphine in carbon tetrachloride at elevated temperature.

Compounds of formula (XIV) may be prepared by reacting the appropriate p-hydroxyaniline, or a protected derivative thereof, with the appropriate acid chloride or anhydride, i.e. $R^6$—COCl or $R^6$—CO.O.CO—$R^6$, for example trifluoroacetic anhydride or cyclopropane carbonyl chloride.

Compounds of formula (XI) where $R^2$ is a group (A) as defined hereinbefore and x is zero, or protected derivatives thereof, may alternatively be prepared by reacting compounds of formula (XIV), or protected derivatives thereof, with an acid anhydride such as trifluoroacetic anhydride or trifluoromethane sulfonic anhydride and sodium azide in acetonitrile.

Compounds of formula (III) where $R^2$ is a group (A) as defined hereinbefore, x is zero and $R^6$ is —NH$_2$ may alternatively be prepared by reacting compounds of formula (XV)

 (XV)

or a protected derivative thereof, with ammonium chloride and sodium azide at elevated temperature, suitably in a solvent such as dimethylformamide, followed by deprotection where required.

Compounds of formula (XV) may be prepared by reacting compounds of formula (III) where $R^2$ is a group (A) as defined hereinbefore, x is zero and $R^6$ is hydrogen, or a protected derivative thereof, with n-butyl lithium in a suitable solvent such as tetrahydrofuran.

Compounds of formula (III), or protected derivatives thereof, where $R^6$ represents one group may be converted into other compounds of formula (III), or protected derivatives thereof, where $R^6$ represents a different group using conventional procedures, such as alkylation, acylation or oxidation.

Compounds of formula (III) may alternatively be prepared by oxidising compounds of formula (XVI)

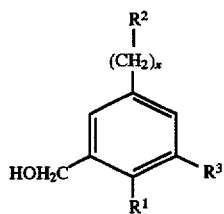 (XVI)

with a suitable oxidising agent such as manganese dioxide in a suitable solvent such as an ether, e.g. tetrahydrofuran, at elevated temperature.

Compounds of formula (XVI) may be prepared by reducing compounds of formula (XVII)

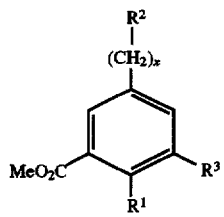 (XVII)

with a suitable reducing agent such as a metal hydride complex such as lithium borohydride in a suitable solvent such as an ether, e.g. tetrahydrofuran, or an alcohol, e.g. ethanol, or a mixture thereof.

Compounds of formula (XVII) where $R^2$ is a group (A) as defined hereinbefore and x is zero may be prepared from the corresponding 2-alkoxy-5-amino benzoic acid methyl ester by reacting with compounds of formula (XII) as defined above, e.g. triethyl orthoformate, and sodium azide in glacial acetic acid and dimethylformamide at elevated temperature.

Suitable 2-alkoxy-5-amino benzoic acid methyl esters are either known or may be prepared according to methods known for the preparation of known compounds e.g. the method described by Bergman et al in Can. J. Chem, (1973), 51, 162–70.

Compounds of formula (III) where $R^2$ is a group (A) or (B) as defined hereinbefore and x is 1, may be prepared by reading compounds of formula (XVIII)

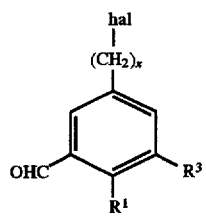 (XVIII)

(where hal is a halogen, e.g. bromine or chlorine, atom) with tetrazole in the presence of a base such as triethylamine or potassium carbonate in a suitable solvent such as dichloromethane or dimethylformamide.

Compounds of formula (XVIII) where x is 1 may be prepared by reacting compounds of formula (XIX)

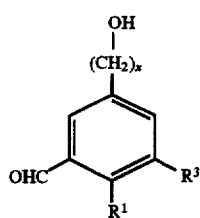 (XIX)

or a protected derivative thereof, with a carbon tetrahalide, e.g. carbon tetrabromide, in the presence of triphenylphosphine and a suitable solvent such as ether, followed by deprotection where required.

Compounds of formula (XIX) may be prepared by reduction of the corresponding aldehydes after protection of the aldehyde group ortho to $R^1$.

Compounds of formula (XI) where $R^2$ is a group (B) and x is zero may be prepared by reading the appropriate 1-fluoro-4-nitrobenzene with IH-tetrazole in a suitable solvent at elevated temperature, followed by reduction of the nitro group by catalytic hydrogenation, followed by conversion of the resulting amino function into an alcohol function using nitrous acid.

Compounds of formula (III) where $R^2$ is a group (C) as defined hereinbefore may be prepared by reading a compound of formula (XX)

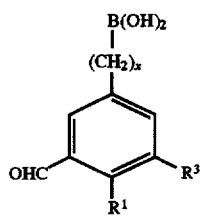 (XX)

with a compound of formula (XXI)

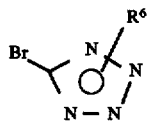 (XXI)

in the presence of a palladium (O) catalyst such as tetrakis(triphenylphosphine) palladium (O) in a suitable solvent such as an ether (e.g. dimethoxyethane) at an elevated temperature.

Compounds of formula (XX) may be prepared according to similar methods for the preparation of compounds of formula (V) above.

Alternatively, compounds of formula (III) where $R^2$ is a group (C) as defined hereinbefore, x is zero and $R^6$ is hydrogen may be prepared by reacting compounds of formula (XXII)

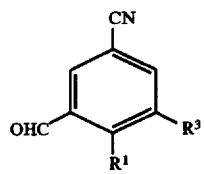 (XXII)

or a protected derivative thereof, with tributyltinazide at elevated temperature, followed by deprotection where necessary.

Compounds of formula (XXII) may be prepared from the appropriate p-hydroxybenzonitrile and hexamethylenetetramine as described above for the preparation of compounds of formula (X) from compounds (XI).

According to a further general process (B), compounds of formula (I) where $R^2$ is a group (A) as defined hereinbefore, x is zero and $R^6$ is $-NH_2$ may be prepared by reacting compounds of formula (XXIII)

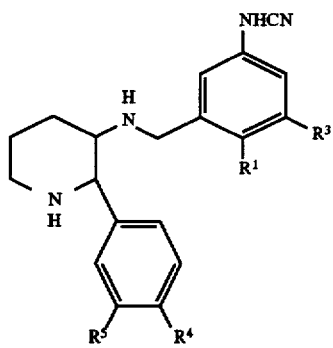 (XXIII)

with ammonium chloride and sodium azide under conditions as described above for the preparation of compounds of formula (III) from compounds of formula (XV).

Compounds of formula (XXIII) may be prepared by reacting compounds of formula (XV) with compounds of formula (II) under conditions as described above for process (A).

According to a further general process (C), compounds of formula (I) may be prepared by reduction of compounds of formula (XXIV)

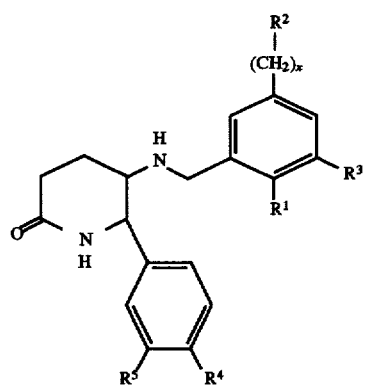 (XXIV)

with a suitable reducing agent, such as a metal hydride, for example a borane hydride, in a suitable solvent such as an ether, e.g. tetrahydrofuran, at ambient temperature.

Compounds of formula (XXIV) may be prepared by reacting compounds of formula (III) with compounds of formula (XXV)

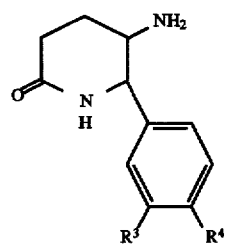 (XXV)

under conditions as described above for process (A).

Compounds of formula (XXV) are either known or may be prepared according to methods known for the preparation of known compounds, for example according to the method described in European Patent Application No. EP-A-0436334, incorporated herein by reference.

Suitable protecting groups for the hydroxyl function include benzyl groups which may be introduced and removed according to conventional procedures. For example deprotection may be effected by catalytic hydrogenation.

Aldehyde functions may be protected as acetals which may be introduced and removed according to conventional procedures. For example, deprotection may be effected by acid hydrolysis.

Compounds of formulae (III), (IV), (X), (XI), (XIII), (XIV), (XV), (XVI), (XVII), (XXIII) and (XXIV), am novel and therefore form a further feature of the invention.

Compounds of formulae (XXIII) and (XXIV) as well as being useful as intermediates for the preparation of compounds of formula (I) have activity as antagonists of tachykinins in their own right and their use in therapy therefore forms a further feature of the invention.

Where it is desired to isolate a compound of formula (I) as a salt, for example a pharmaceutically acceptable salt, this may be achieved by reacting the compound of formula (I) in the form of the free base with an appropriate amount of suitable acid and in a suitable solvent such as an alcohol (e.g. ethanol or methanol), an ester (e.g. ethyl acetate) or an ether (e.g. diethyl ether or tetrahydrofuran).

Pharmacautically acceptable salts may also be prepared from other salts, including other pharmaceutically acceptable salts, of the compound of formula (I) using conventional methods.

The compounds of formula (I) may readily be isolated in association with solvent molecules by crystallisation from or evaporation of an appropriate solvent to give the corresponding solvates.

When a specific enantiomer of a compound of general formula (I) is required, this may be obtained for example by resolution of a corresponding enantiomeric mixture of a compound of formula (I) using conventional methods.

Thus, in one example an appropriate optically active acid may be used to form salts with the enantiomeric mixture of a compound of general formula (I). The resulting mixture of isomeric salts may be separated for example by fractional crystallisation, into the diastereoisomeric salts from which the required enantiomer of a compound of general formula (I) may be isolated by conversion into the required free base.

Alternatively, enantiomers of a compound of general formula (I) may be synthesised from the appropriate optically active intermediates using any of the general processes described herein.

A particularly suitable route for the preparation of optically active intermediates of formula (II) from the enantiomeric mixture thereof is by fractional crystallisation using (2R, 3R)-bis-(4-methyl-benzoyloxy)-succinic acid. Thus, the cis (S,S) form of intermediate (II) may be obtained from an enantiomeric mixture thereof (e.g. the racemic mixture) by fractional crystallisation with (2R, 3R)-bis-(4-methylbenzoyloxy)-succinic acid in a suitable solvent, such as an aqueous alcohol, e.g. aqueous ethanol, isolating the resulting salt and converting it into the corresponding optically active free base by conventional procedures for example using aqueous ammonia. Such a process is novel and forms a further feature of the invention.

Salts formed between intermediate (II), including 2-phenyl-piperidin-3-ylamine, and (2R, 3R)-bis-(4-methylbenzoyloxy)-succinic acid are novel and form a further feature of the invention.

Specific enantiomers of a compound of formula (I) may also be obtained by chromatography of the corresponding enantiomeric mixture on a chiral column, for example by chiral preparative h.p.l.c.

Specific diastereoisomers of a compound of general formula (I) may be obtained by conventional methods for example, by synthesis from an appropriate asymmetric starting material using any of the processes described herein, or by conversion of a mixture of isomers of a compound of general formula (I) into appropriate diastereoisomeric derivatives e.g. salts which can then be separated by conventional means e.g. by chromatography or by fractional crystallisation.

Alternatively, the diastereosiomers may be separable without the need for further derivatization.

Standard resolving methods are described for example in 'Stereochemistry of Carbon Compounds' by E. L. Eliel (McGraw Hill, 1962) and 'Tables of Resolving Agents' by S. H. Wilen.

The various general methods described above may be useful for the introduction of the desired groups at any stage in the stepwise formation of the required compound, and it will be appreciated that these general methods can be combined in different ways in such multi-stage processes. The sequence of the reactions in multi-stage processes should of course be chosen so that the reaction conditions used do not affect groups in the molecule which are desired in the final product.

The invention is further illustrated by the following Intermediates and Examples which are not intended as a limitation of the invention. All temperatures are in °C. Flash column chromatography (FCC) was carried out on silica (Merck 9385). The following abbreviations are used: ether-diethyl ether.

INTERMEDIATE 1

4-Tetrazol-1-yl-phenol

To a stirred solution of p-amino-phenol (0.1 mol) in glacial acetic acid (140 ml) at 70°–75° under nitrogen atmosphere was added triethylorthoformate (0.1 mol). The mixture was stirred at this temperature for 4 h, then, sodium azide (0.32 mol) was added portionwise and the reaction was continued for 18 h, cooled to room temperature and poured into ice water (400 ml) and extracted with diethyl ether (3×400 ml) and ethyl acetate (1×400 ml), dried ($MgSO_4$), filtered and concentrated to give a dark brown residue which was triturated with 200 ml of a mixture of ethanol:diethyl ether (1:1 v/v) and filtered to afford the title compound in 30% yield. T.l.c. (ether) Rf 0.65

Similarly prepared:

INTERMEDIATE 2

4-(5-Methyl-tetrazol-1-yl)-phenol

From p-amino phenol (0.05 mol), triethylorthoacetate (0.05 mol) and sodium azide (0.16 mol) to afford the title compound as a dark brown solid in 8% yield. T.l.c. (ether) Rf 0.8

INTERMEDIATE 3

4-(5-Ethyl-tetrazol-1-yl)-phenol

From p-aminophenol (0.05 mol), triethylorthopropionate (0.05 mol) and sodium azide (0.16 mol) to afford the title compound as a dark brown solid in 9% yield. T.l.c. (ether) Rf 0.72

INTERMEDIATE 4

4-(5-Propyl-tetrazol-1-yl)-phenol

From p-aminophenol (6 g), trimethylorthobutyrate (8.1 g) and sodium azide (10 g) to afford the title compound as a dark brown liquid, (0.55 g). T.l.c. (ether/dichloromethane (1:9)), Rf 0.27

INTERMEDIATE 5

2-Hydroxy-5-tetrazol-1-yl-benzaldehyde

A solution of 4-tetrazol-1-yl-phenol (0.01 mol) in trifluoroacetic add (20 ml) and hexamethylenetetramine (0.04 mol) was heated at 70° for 18 h, cooled to room temperature and quenched with 2N solution of sulfuric acid (50 ml). The mixture was extracted with ethyl acetate (3×100 ml), dried (MgSO$_4$), filtered and concentrated to give a residue which was purified by FCC (dichloromethane/methanol (9:1)) to afford the title compound in 30% yield. T.l.c. (dichlormethane/methanol (9:1)) Rf 0.6

Similarly prepared:

INTERMEDIATE 6

2-Hydroxy-5-(5-methyl-tetrazol-1-yl)-benzaldehyde

From 4-(5-methyl-tetrazol-1-yl)-phenol (3.97 mmol), to give the title compound (70% yield) as a pale yellow solid. T.l.c. (dichloromethane/methanol (9:1)) Rf 0.9

INTERMEDIATE 7

5-(5-Ethyl-tetrazol-1-yl)-2-hydroxy-benzaldehyde

From 4-(5-ethyl-tetrazol-1-yl)-phenol (4.73 mmol) to give the title compound in 50% yield as a white solid. T.l.c. (dichloromethane/methanol (9:1)) Rf 0.9.

INTERMEDIATE 8

2-Hydroxy-5-(5-propyl-tetrazol-1-yl)-benzaldehyde

From 4-(5-propyl-tetrazol-1-yl)-phenol (0.55 g) to give the title compound (0.3 g) as a pale yellow liquid. T.l.c. (ether/dichloromethane (1:9)), Rf 0.41

INTERMEDIATE 9

5-(5-Cyclopropyl-tetrazol-1-yl)-2-hydroxy-benzaldehyde

From 4-(5-cyclopropyl-tetrazol-1-yl)-phenol (1.5 g) to give the title compound (810 mg) as a white solid, m.p. 96°.

INTERMEDIATE 10

2-Hydroxy-5(5-methylsulfanyl-tetrazol-1-yl)-benzaldehyde

From 4-(5-methylsulfanyl-tetrazol-1-yl)-phenol (10.64 g) to give the title compound as a white solid (5.0 g). T.l.c. (Dichloromethane), Rf=0.35

INTERMEDIATE 11

2-Hydroxy-5-(5-phenyl-tetrazol-1-yl)-benzaldehyde

From 4-(5-phenyl-tetrazol-1-yl)-phenol (2.32 g) to give the title compound as a white solid (1.75 g). T.l.c. (5% Ethyl acetate/dichloromethane), Rf 0.6.

INTERMEDIATE 12

3-Fluoro-2-hydroxy-5-(5-methyl-tetrazol-1-yl)-benzaldehyde

From 2-fluoro-4-(5-methyl-tetrazol-1-yl)-phenol (2.8 g) to give the title compound as a white solid (2.2 g). T.l.c. (Cyclohexane/ethyl acetate (1:1)), Rf 0.7.

INTERMEDIATE 13

2-Hydroxy5(5-trifluoromethyl-tetrazol-1-yl)-benzaldehyde

From 4-(5-trifluoromethyl-tetrazol-1-yl)-phenol (45 mmol) to give the title compound (8.8 g) as a pale yellow solid. T.l.c. (Hexane/ether (2:1)) Rf 0.36

INTERMEDIATE 14

2-Methoxy-5-tetrazol-1-yl-benzaldehyde

To a solution of 2-hydroxy-5-tetrazol-1-yl-benzaldehyde (2.63 mmol) in dimethylformamide (5 ml) was added potassium carbonate (3.95 mmol) and iodomethane (3.95 mmol) and the mixture was stirred under nitrogen atmosphere for 2 h. The mixture was poured into water (100 ml) and the white solid formed filtered to afford the title compound in a 67% yield. T.l.c. (ether) Rf 0.45

Similarly prepared:

INTERMEDIATE 15

2-Methoxy-5-(5-methyl-tetrazol-1-yl)-benzaldehyde

From 2-hydroxy-5-(5-methyl-tetrazol-1-yl)-benzaldehyde (2.79 mmol) to give the title compound in 42% yield as white needles. T.l.c. (dichloromethane./methanol (9:1)) Rf 0.5

INTERMEDIATE 16

5-(5-Ethyl-tetrazol-1-yl)-2-methoxy-benzaldehyde

From 5-(5-ethyl-tetrazol-1-yl)-2-hydroxy-benzaldehyde (2.84 mmol) to give the title compound in 67% yield as a white solid. T.l.c. (ether) Rf 0.4

INTERMEDIATE 17

2-Methoxy-5-(5-propyl-tetrazol-1-yl)-benzaldehyde

From 2-hydroxy-5-(5-propyl-tetrazol-1-yl)-benzaldehyde (300 mg) to give the title compound (265 mg) as a white solid. T.l.c. (ether) Rf 0.27.

INTERMEDIATE 18

5-(5-Cyclopropyl-tetrazol-1-yl)-2-methoxy-benzaldehyde

From 5-(5-cyclopropyl-tetrazol-1-yl)-2-hydroxy-benzaldehyde (800 mg) to give the title compound (800 mg) as a white solid, m.p. 142°.

INTERMEDIATE 19

2-Methoxy-5-(5-methylsulfanyl-tetrazol-1-yl)-benzaldehyde

From 2-hydroxy-5-(5-methylsulfanyl-tetrazol-1-yl)-benzaldehyde (5.0 g) to give the title compound as a yellow solid (2.1 g). T.l.c. (Ethyl acetate), Rf=0.8

INTERMEDIATE 20

2-Methoxy-5-(5-phenyl-tetrazol-1-yl)-benzaldehyde

From 2-hydroxy-5-(5-phenyl-tetrazol-1-yl)-benzaldehyde (0.636 g) to give the title compound as a yellow solid (0.575 g). T.l.c. (5% ethyl acetate/dichloromethane), Rf 0.55.

INTERMEDIATE 21

2-Methoxy-5-(5-methylimino-4,5-dihydro-tetrazol-1-yl)-benzaldehyde

From 1-(3-[1,3]dioxolan-2-yl-4-methoxy-phenyl)-1H-tetrazol-5-ylamine (0.5 g) to give the title compound as a solid (0.15 g). T.l.c. (5% methanol/dichloromethane). Rf 0.6.

INTERMEDIATE 22

3-Fluoro-2-methoxy-5-(5-methyl-tetrazol-1-yl)-benzaldehyde

From 3-fluoro-2-hydroxy-5-(5-methyl-tetrazol-1-yl)-benzaldehyde (2.2 g) to give the title compound as a cream solid (1.5 g). T.l.c. (Ethyl acetate/cyclohexane (1:1)), Rf=0.4.

INTERMEDIATE 23

2-Methoxy-5-(5-trifuoromethyl-tetrazol-1-yl)-benzaldehyde

From 2-hydroxy-5-(5-trifluoromethyl-tetrazol-1-yl)-benzaldehyde (1.56 mmol) to give the title compound as a yellow solid (0.48 g). T.l.c. (ether/hexane (2:1)) Rf 0.38.

INTERMEDIATE 24

2-Ethoxy-5-tetrazol-1-ylbenzaldehyde

From ethyl iodide and 2-hydroxy-5-tetrazol-1-ylbenzaldehyde (2.6 mmol) to give the title compound (0.52 g) as a yellow solid. vmax (KBr) 1677 $cm^{-1}$.

INTERMEDIATE 25

2-Isopropoxy-5-tetrazol-1-ylbenzaldehyde

From isopropyl iodide and 2-hydroxy-5-tetrazol-1-ylbenzaldehyde (2.6 mmol) to give the title compound (0.40 g) as a yellow solid. vmax (KBr) 1681 $cm^{-1}$.

INTERMEDIATE 26

[2S]-Phenyl-piperidin-[3S]-yl-amine[2R,3R]-bis(4-methyl-benzoyloxy-succinate (1:1)

(2R,3R)-bis-(4-methyl-benzoyloxy)-succinic acid (143 g) was added portionwise over 5 min. to a stirred solution of racemic 2-phenyl-piperidin-3-ylamine (66 g) in ethanol (5.2l) and water (783 ml) at 60°. The solution was then allowed to stir for 0.5 h at a temperature between 60°–70°. The solution was allowed to cool overnight at ambient temperature. The solid material was collected and dried in vacuo at 70° (80 g). A sample (10 g) was recrystallised from ethanol (510 ml) and water (90 ml) to give a near colourless crystalline solid (7.6 g) m.p. 169°–171°

Found: C,62.6; H, 6.2; N,4.5 $C_{11}H_{16}N_2 \cdot C_{20}H_{18}O_8 \cdot 2H_2O$ requires: C,62.2; H,6.4; N, 4.7%.

$[\alpha]^2{}_D\alpha=+34.3°$

Similarly prepared:

INTERMEDIATE 27

2S-(4-Fluoro-phenyl)-piperidin-3S-ylamine-2R,3R-bis-(4-methyl-benzoyloxy)-succinate From racemic 2-(4-Fluorophenyl)-piperidin-3-ylamine (1.0 g) and (2R,3R)-bis-(4-methyl-benzoyloxy)-succinic acid (2.0 g) to give the title compound as white crystalline solid (803.5 mg). δ ($CD_3OD$) includes 1.5–2.2 (m, 5H), 2.4 (s, 6H), 2.85–3.05 (m, 1H), 3.5–3.6 (m, 1H), 4.27 (d, 1H, J=2 Hz), 5.86 (s, 2H), 7.0(t,2H, J=8.7 Hz), 7.3 (d, 4H, J=8.5 Hz), 7.45 (dd, 2H, J=8.7 and 5 Hz). Chiral HPLC on a CHIRALCEL-OD-H column eluting with hexane containing 2% isopropyl alcohol showed only one enantiomer ($t_R$=35.83 mins). T.l.c. (cyclohexane/ethylacetate (9:1)) Rf 0.36

INTERMEDIATE 28

[2S]-Phenyl-piperidin-[3S]-ylamine

[2S]-Phenyl-piperidin-[3S]-ylamine [2S,3S]-bis(4-methyl-benzoyloxy)-succinic acid salt (1:1) (6.9 g) was taken up in concentrated 0.880 aqueous ammonia solution (100 ml) and shaken for a few minutes. The basic solution was extracted with chloroform (3×150 ml), dried ($Na_2SO_4$), and concentrated in vacuo to give [2S]-phenyl-piperidin-[3S]-ylamine (1.85 g) as a colourless oil.

$[\alpha]^{20}{}_D$ (HCl salt)=+65.48° (C=0.006 g/ml)

$^1$H NMR (HCl salt, $D_2O$) δ 2.05 (m, 2H), 2.30 (m, 2H), 3.36 (m, 1H), 3.74 (m, 1H), 4.16 (q, 1H, J=4 Hz), 4.99 (d, 1H, J=4 Hz), 7.45 (m, 2H), 7.59 (m, 3H).

A small sample of the free base (50 mg) was dedvatized as its trifluoroacetyl analogue for chiral HPLC analysis. The sample was dissolved in acetonitrile (4 ml) and treated with 1-(trifluoroacetyl)imidazole (0.4 ml). The solution was stirred at 65° for 1 h, concentrated in vacuo and the residue dissolved in dichloromethane (5 ml). The organic layer was washed with dilute sulphuric acid (2 ml), then the organic layer concentrated and disssolved in hexane-isoproplyalcohol (98:2) for injection onto the HPLC column. Chiral HPLC (Chiracel-OD-H column, lot no. 09-02-20709, eluent hexane-isopropylalcohol 98:2, flow rate 1 ml/min, detection uv 230 nm, temperature 40°) retention time 12.93 mins.

INTERMEDIATE 29

N-(4-Benzyloxy-phenyl)-2,2,2-trifluoro-acetamide

A mixture of 4-benzyloxyaniline hydrochloride (0.19 mol) in dichloromethane (750 ml) at 0° under nitrogen was treated dropwise with trifluoroacetic anhydride (27.6 ml) then triethylamine (60 ml). After 24 h the mixture was poured into t-butyl methyl ether (1.5 l) and was washed with 2N hydrochloric acid (1 l). The organic phase was dried ($MgSO_4$) and evaporated in vacuo to give the title compound as a white solid (52.3 g). T.l.c. (cyclohexane/ethylacetate (9:1)) Rf 0.36.

INTERMEDIATE 30 trans-6-(3-Bromo-phenyl)-5-nitro-piperidin-2-one

A mixture of 3-bromobenzaldehyde (82.20 g), methyl-4-nitrobutyrate (65.3 g) and ammonium acetate (68.5 g) in ethanol (400 ml), was heated to reflux for 18 hours. The solvent was removed in vacuo and the resultant mixture triturated with ethanol (400 ml) to give the title compound as a white solid (97.46 g). NMR ($CDCl_3$) δ 2.30 (1H, m), 2.55 (3H, m), 4.70 (1H, m), 5.25 (1H, m), 6.7 (1H, s), 7.2–7.6 (4H, m).

Similarly prepared:

INTERMEDIATE 31 trans-6-(4-Methoxy-phenyl)-5-nitro-piperidin-2-one

From p-anisaldehyde (5 g) and methyl 4-nitrobutyrate (5.4 g) to give the title compound (7.37 g) as a white powder. T.l.c. (Ethyl acetate), Rf 0.35.

23

INTERMEDIATE 32 trans-6-(3-Bromo-4-methyl-phenyl)-5-nitro-piperidin-2-one

From 3-bromo-4-methylbenzaldehyde (30 g) and methyl-4-nitrobutyrate (22.17 g) to give the title compound (24.5 g) as a brown powder. T.l.c. (Ethyl acetate) Rf 0.4

INTERMEDIATE 33

6-(3-Chloro-phenyl)-5-nitro-piperidin-2-one

From 3-chlorobenzaldehyde (5 g) and methyl-4-nitrobutyrate (5.23 g) to give the title compound (6.84 g) as a white powder. T.l.c. (Ethyl acetate), Rf 0.55.

INTERMEDIATE 34

6-(3-Bromo-phenyl)-piperidine-2,5-dione

Potassium t-butoxide (38.7 g) was added to a stirred solution of the trans-6-(3-bromo-phenyl)-5-nitro-piperidin-2-one (96.3 g) in dichloromethane (500 ml) and methanol (500 ml). The mixture was cooled to −70° and ozone was vigorously bubbled through the stirred solution for 7 h. The mixture was purged with nitrogen and pH6.5 phosphate buffer (500 ml) added. Sodium thiosulphate (120 g) and water (500 ml) were added and the mixture stirred as it warmed to room temperature overnight. The mixture was tested for peroxides then extracted with dichloromethane (600 ml×3). The combined organic extracts were washed with water (500 ml) then saturated brine (500 ml), dried ($MgSO_4$) and evaporated in vacuo. Trituration with ether and hexane gave the title compound as a white solid (70.0 g). T.l.c. (Ethyl acetate) Rf 0.43.

Similarly prepared:

INTERMEDIATE 35

6-(4-Methoxy-phenyl)-piperidine-2,5-dione

From trans-6-(4-methoxy-phenyl)-5-nitro-piperidin-2-one (7.37 g) to give the title compound (5.53 g) as a yellow powder. T.l.c. (Ethyl acetate), Rf 0.3.

INTERMEDIATE 36

6-(3-Bromo-4-methyl-phenyl-piperidin-2,5-dione

From trans-6-(3-bromo-4-methyl-phenyl)-5-nitro-piperidin-2-one (24.5 g) to give the title compound (19.9 g) as a brown oil. T.l.c. (Ethyl acetate) Rf 0.45.

INTERMEDIATE 37

6-(3-Chloro-phenyl)-piperidin-2,5-dione

From 6-(3-chloro-phenyl)-5-nitro-piperidin-2-one (6.8 g) to give the title compound (5.27 g) as a white solid. T.l.c. (Ethyl acetate), Rf 0.47.

INTERMEDIATE 38

6-(3-Bromo-phenyl)-piperidine-2,5-dione 5-oxime

A mixture of 6-(3-bromo-phenyl)-piperidine-2,5-dione (38.2 g) and hydroxylamine hydrochloride (19.8 g) in pyridine (300 ml) was stirred at room temperature under nitrogen. After 4 h the mixture was evaporated in vacuo. The crude mixture was partitioned between chloroform (200 ml) and water (200 ml) then was basified by the addition of 8% sodium bicarbonate solution (~300 ml). The mixture was extracted with chloroform (300 ml×2). The combined organic extracts were washed with saturated brine and evaporated in vacuo. Trituration with ether gave the title compound as a pale yellow solid (34.9 g). T.l.c. (Ethyl acetate) Rf 0.44, 0.28, E/Z mixture.

Similarly prepared:

INTERMEDIATE 39

6-(4-Methoxy-phenyl)-piperidin-2,5-dione 5-oxime

From 6-(4-methoxy-phenyl)-piperidine-2,5-dione (5.27 g) and hydroxylamine (3.34 g) to give the title compound (4.38 g) as a pale brown powder. T.l.c.(Ethyl acetate), Rf 0.34, 0.21.

INTERMEDIATE 40

6-(3-Bromo-4-methyl-phenyl)-piperidine-2,5-dione-5-oxime

From 6-(3-bromo-4-methyl-phenyl)-piperidine-2,5-dione (19.7 g) and hydroxylamine hydrochloride (9.77 g) to give the title compound (6.37 g) as a yellow solid. T.l.c. (Ethyl acetate) Rf 0.56.

INTERMEDIATE 41

6-(3-Chloro-phenyl)-piperidine-2,5-dione 5-oxime

From 6-(3-chloro-phenyl)-piperidine-2,5-dione (5.27 g) and hydroxylamine hydrochloride (3.27 g) to give the title compound (4.57 g) as a yellow powder. T.l.c. (Ethyl acetate), Rf 0.55, 0.33 (E/Z mixture).

INTERMEDIATE 42 cis-2-(3-Bromo-phenyl)-piperidin-3-ylamine

Dry tetrahydrofuran (100 ml) was added to a flask containing zirconium (IV) chloride (6.17 g) cooled to 0° under nitrogen. Sodium borohydride (4.0 g) was added and the mixture stirred as it warmed to room temperature over 15 mins. A suspension of 6-(3-bromo-phenyl)-piperidine-2,5-dione 5-oxime (×g) in dry tetrahydrofuran (50 ml) was added dropwise and the mixture was stirred at room temperature for 18 h. Concentrated hydrochloric acid (10 ml) in methanol (60 ml) was cautiously added and the mixture was heated to reflux for 3 h. The mixture was evaporated in vacuo and the residue was partitioned between 0.88 ammonia (40 ml) in water (200 ml) and chloroform (100 ml). The aqueous phase was extracted with chloroform (100 ml×3). The combined organic extracts were dried ($Na_2SO_4$) and evaporated to an oil. This was dissolved in ethanol (50 ml) and acidified by adding ethereal hydrogen chloride. The solution was evaporated and the residue recrystallised from i-propanol-hexane to give a white solid. The solid was treated with 2N sodium hydroxide solution (200 ml) and extracted with dichloromethane (200 ml×3). The combined organic extracts were dried ($Na_2SO_4$) and evaporated in vacuo to give the title compound as a yellow-brown oil (1.10 g). T.l.c. (Dichloromethane/ethanol/ammonia (91:8:1)) Rf 0.51.

Similarly prepared:

INTERMEDIATE 43 cis-2-(4-Methoxy-phenyl)-piperidin-3-ylamine dihydrochloride

From 6-(4-Methoxy-phenyl)-piperidine-2,5-dione 5-oxime (4.18 g) to give the title compound (2.07 g) as a white powder. T.l.c. (Dichloromethane/ethanol/ammonia (150:8:1)) Rf 0.1.

INTERMEDIATE 44 cis-2-(3-Bromo-4-methyl-phenyl)-piperidin-3-ylamine

From 6-(3-Bromo-4-methyl-phenyl)-piperidine-2,5-dione (6.2 g) to give the title compound (2 g) as a yellow oil. T.l.c. (Dichloromethane/ethanol/ammonia (150:8:1)) Rf 0.3.

INTERMEDIATE 45 cis 2-(3-Chloro-phenyl)-piperidin-3-ylamine dihydrochloride

From 6-(3-Chloro-phenyl)-piperidine-2,5-dione 5-oxime (4.55 g) to give the title compound (361 mg) as a white solid. T.l.c. (Dichloromethane/ethanol/ammonia (100:8:1)) Rf 0.49.

INTERMEDIATE 46

2-(3-Fluoro-4-methylphenyl)-3-nitropyridine

A solution of 2-chloro-3-nitropyridine (4.24 g) in dimethoxyethane (47 ml, degassed) was treated with tetrakis (triphenyl phosphine)palladium (O) (1.547 g) under nitrogen and the resulting solution was stirred at room temperature for 0.75 h. The solution was treated with 3-fluoro-4-methylphenylboronic acid (6.179 g) in ethanol (24 ml, degassed), followed by aqueous sodium carbonate solution (2M, 47 ml) to give a light yellow suspension which was heated at reflux for 5 h. After cooling to room temperature, the reaction mixture was diluted with ethyl acetate (100 ml). The resulting mixture was filtered and the filtrate was washed with water (2×100 ml) and saturated aqueous sodium bicarbonate solution (150 ml). The organic layer was separated and the aqueous solution was extracted further with ethyl acetate. The combined organic portions were washed with brine (100 ml), dried (MgSO$_4$) and evaporated to give a red-black oil (12.106 g). FCC (cyclohexane-ethyl acetate; 4:1) gave the title compound as a yellow solid (5.55 g). Microanalysis for $C_{12}H_9FN_2O_2$, calcd. C, 62.07; H, 3.91; N, 12.07; F, 8.18%. Found: C, 61.58; H, 3.92; N, 11.80; F, 8.2%.

Similarly prepared:

INTERMEDIATE 47

2-(3-Fluorophenyl)-3-nitropyridine

From 2-chloro-3-nitropyridine (6.371 g) and 3-fluorophenylboronic acid (8.30 g) to give the title compound as a yellow crystalline solid (3.39 g). δ (d$^6$-DMSO), 7.40–7.56 (m, 3H), 7.59–7.69 (m, 1H), 7.83 (dd, 1H, J=8 and 5 Hz), 8.60 (dd, 1H, J=7.5 and 1.0 Hz), 9.04 (dd, 1H, J=4.5 and 1.5 Hz).

INTERMEDIATE 48

2-(4-Fluorophenyl)-3-nitropyridine

From 2-chloro-3-nitropyridine (4.60 g) and 4-fluorophenylboronic acid (5.99 g) to give the title compound as a yellow solid (5.07 g). δ (d$^6$-DMSO) 7.35 (t, 2H, J=8.5 Hz), 7.62 (dd, 2H, J=8.5 and 5.5 Hz), 7.71 (dd, 1H, J=8.0 and 5.0 Hz), 8.48 (d, 1H, J=8.0 Hz), 8.94 (d, 1H, J=5.0 Hz).

INTERMEDIATE 49

2-(3,4-Difluorophenyl)-3-nitropyridine

From 2-chloro-3-nitropyridine (2.24 g) and 3,4-difluorophenyl-boronic acid (2.90 g) to give the title compound (2.84 g). δ (d$^6$-DMSO) 7.46–7.55 (m, 1H), 7.62–7.89 (m, 3H), 8.64 (dd, 1H, J=7.5 and 1 Hz), 9.06 (d, 1H, J=4.5 Hz).

INTERMEDIATE 50 cis-2-(3-Fluoro-4-methylphenyl)-3-piperidinamine

A solution of 2-(3-fluoro-4-methylphenyl)-3-nitropyridine (5.514 g) in ethanol (200 ml) was cautiously added under nitrogen to platinum oxide (1.592 g) in ethanol (10 ml). The mixture was then treated with concentrated hydrochloric acid (16 ml) and stirred at room temperature under atmospheric pressure of hydrogen for 16 h. The reaction was diluted with water (150 ml) and filtered and the filtrate was evaporated to give a pale yellow solid which was then suspended between chloroform (200 ml) and water (200 ml) with good stirring. Concentrated ammonia solution was added until the aqueous phase reached ca. pH9. The organic phase was separated, and the aqueous phase was extracted with chloroform (2×150 ml). The combined organic portions were washed with brine, dried (MgSO$_4$) and the solvent was evaporated to give a clear yellowish brown oil (4.316 g). FCC (dichloromethane:methanol:concentrated ammonia, 95:4:1) gave the title compound as a waxy solid (2.584 g). δ (d$^6$-DMSO) 1.3–1.8 (m, 4H), 2.2 (s, 3H). 2.55–2.68(m, 1H), 2.85 (d, 1H, J=2 Hz), 3.01 (dm, 1H, J=12 Hz), 2.7–3.8 (broad s, 2H), 3.68 (s, 1H), 6.97–7.08 (m, 2H), 7.19 (t, 1H, J=8 Hz).

Similarly prepared:

INTERMEDIATE 51 cis-2-(3-Fluorophenyl)-3-piperidinamine

From 2-(3-fluorophenyl)-3-nitropyridine (3.292 g) to give the title compound (0.584 g). Mass Spoctrometry for $C_{11}H_{15}FN_2$, 389 (2M+H$^+$), 195 (MH$^+$).

INTERMEDIATE 52 cis-2-(4-Fluorophenyl-3-piperidinamine

From 2-(4-fluorophenyl)-3-nitropyridine (4.88 g) to give the title compound as a colourless oil (3.08 g). Mass spectrometry. For $C_{11}H_{15}FN_2$, m/z 195 (MH$^+$).

INTERMEDIATE 53 cis-2-(3,4-Difluorophenyl)-3-piperidinamine

From 2-(3,4-difluorophenyl)-3-nitropyridine (2.83 g) to give the title compound as a pale yellow oil (1.69 g). Mass spectrometry. For $C_{11}H_{14}F_2N_2$, m/z 213 (MH$^+$).

INTERMEDIATE 54

3,4-Difluorophenylboronic acid

Magnesium turnings (1.32 g) were stirred under nitrogen for 10 mins then anhydrous tetrahydrofuran (30 ml) followed by 1-bromo-3,4-difluorobenzene (7.0 g) were added over 5 mins. The mixture was maintained at reflux for 30 mins and then allowed to cool to room temperature. A solution of tri-isopropylborate (13.65 g) in dry tetrahydrofuran (80 ml) under nitrogen was cooled to −78° (dry ice-acetone) and the preformed Grignard solution was added over 10 mins. The mixture was stirred for 2 h and then allowed to warm to room temperature over 45 mins. The reaction was quenched with hydrochloric acid (4M, 80 ml) and stirred at room temperature overnight. The solution was extracted with ethyl acetate (3×100 ml) and the combined organic solutions extracted with aqueous sodium hydroxide (1M, 4×100 ml). The combined aqueous basic solutions were acidified to pH3 (4M hydrochloric acid), extracted with ethyl acetate (3×150 ml) and the combined organic fractions washed with acidified brine (200 ml) and dried (MgSO$_4$). Removal of the solvent gave the title compound as a white solid (2.7 g). δ (d$^6$-DMSO+D$_2$O) 7.42 (dt, 1H, J=10.5 and 7.5 Hz), 7.60–7.78 (m, 2H).

INTERMEDIATE 55 trans-5-Nitro-6-(4-trifluoromethyl-phenyl)-piperidin-2-one

Ammonium acetate (21.21 g), 4-trifluoromethylbenzaldehyde (19.61 ml) and methyl 4-nitrobutyrate (17.5 ml) in ethanol (150 ml) was stirred and heated under reflux for 3.5 h. After cooling to room temperature, an orange solid was formed which was filtered, washed with ethanol (2×100 ml) and dried in vacuo to give the title compound (30.56 g). Mass spectrometry. For C$_{12}$H$_{11}$F$_3$N$_2$O$_3$, m/z 5.77 (2M+H$^+$), 306 (M+NH$_4$), 289 (MH$^+$).

INTERMEDIATE 56

6-(4-Trifluoromethyl-phenyl)-piperidine-2,5-dione

Potassium tert-butoxide (8.665 g) was added gradually to a stirring suspension of trans-5-nitro-6-(trifluoromethyl)-phenyl-piperidin-2-one (20.18 g) in a mixture of dichloromethane (100 ml) and methanol (100 ml) at room temperature under nitrogen. An orange solution was formed which was cooled to −70° and ozone was bubbled through the solution for 4 h followed by another 20 mins with nitrogen. Phosphate buffer (pH 6, 200 ml) and sodium thiosulphate (pentahydrate, 25.1 g) were added and the mixture was allowed to warm to room temperature. Extraction with ethyl acetate (4×200 ml) gave a yellow solid (15.82 g) which was purified by FCC (ethyl acetate and then methanol:dichloromethane, 1:15) to give the title compound (8.62 g). δ (d$^6$-DMSO) 2.56–2.67 (m, 2H), 2.68–2.73 (m, 2H), 5.14 (broad d, 1H, J=2 Hz), 7.55 and 7.77 (2d, 4H, J=8 Hz for both), 8.29–8.36 (broad s, 1H).

INTERMEDIATE 57

6-(4-Trifluoromethyl-phenyl)-piperdin-2,5-dione 5-oxime

Pyridine (47 ml) and hydroxylamine hydrochloride (8.18 g) were added to a stirring solution of 6-(4-trifluoromethyl-phenyl)-piperidin-2,5-dione (5.04 g) under nitrogen. The mixture was heated at reflux for 21 h, cooled to room temperature, poured into aqueous hydrochloric acid (2M, 100 ml) and extracted with ethyl acetate (100 ml). The organic extract was washed with aqueous hydrochloric acid (3×100 ml) and the combined aqueous solution was extracted with ethyl acetate (2×50 ml). The combined organic solution was dried (MgSO4) and evaporated in vacuo to give the crude product (5.84 g) which was azeotroped with toluene (3×50 ml). FCC (dichloromethane:methanol, 12:1) gave the title compound (3.26 g) as an inseparable mixture of geometrical isomers (2:1). δ (d$^6$-DMSO) for the major isomer: 2.0–2.4 (m, 4H), 5.15 (d, 1H, J=3.5 Hz), 7.49 and 7.75 (2d, 4H, J=8 Hz for both). 8.39 (d, 1H, J=3.5 Hz), 11.08 (s, 1H). $^1$H-NMR signals for the minor isomer includes 5.77 (d, 1H, J=2.5 Hz), 7.59 and 7.72 (2d, 4H, J=8 Hz for both), 8.10 (d, 1H, J=2.5 Hz), 11.14 (s, 1H).

INTERMEDIATE 58 cis-5-Amino-6-(4-trifluoromethyl-phenyl)-piperidin-2-one 6-(4-Trifluoromethylphenyl)piperidin-2,5-one, 5-oxime (2.6 g) was dissolved in a mixture of methanol (15 ml) and ethanol (60 ml) and added to Raney nickel [50% suspension in water, 5.05 g, washed with water (2×25 ml) and ethanol (25 ml)] under nitrogen. The mixture was hydrogenated under 50 psi of hydrogen pressure for 40 h at room temperature and then filtered. The filtrate was evaporated in vacuo to give the crude product (2.43 g). FCC (10% concentrated ammonia) followed by the same solvent system containing 0.5% concentrated ammonia) gave the title compound (1.262 g). Mass spectrometry. For C$_{12}$H$_{13}$F$_3$N$_2$O, m/z 259 (MH$^+$).

INTERMEDIATE 59

[4Methoxy-3-(2S-phenyl-piperidin-3S-ylaminomethyl)-phenyl]-cyanamide dihydrochloride To a suspension of (3-formyl-4-methoxy-phenyl)-cyanamide (0.238 g) in dichloromethane (10 ml), 2S-phenyl-piperidin-3S-ylamine (0.225 g), sodium triacetoxyborohydride (0.5 g) and acetic acid (0.14 ml) were added and the mixture stirred at room temperature under an atmosphere of nitrogen for 18 h. The resulting solution was treated with 8% aqueous sodium bicarbonate solution (20 ml) and extracted with dichloromethane (3×30 ml). The combined organic layers were then dried (Na$_2$SO$_4$) and evaporated in vacuo. The resulting residue was purified by column chromatography eluting with dichloromethane:ethanol:ammonia (100:10:5). The oily product was dissolved in dichloromethane (10 ml) and treated with hydrogen chloride solution (3 ml of 1M in ether) to give a precipitated solid. The solvents were removed and the material dried in vacuo to yield the title compound as a white solid (0.175 g), m.p. 255°–8° (dec.).

Similarly prepared:

INTERMEDIATE 60 cis-5-(2-Methoxy-5-tetrazol-1-yl)-benzylamino-6-(4-trifluoromethyl-phenyl)-piperidin-2-one From cis-5-amino-6-(4-trifluoromethyl-phenyl)-piperidin-2-one (404 mg) and 2-methoxy-5-tetrazol-1-yl-benzaldehyde (411 mg), to give the title compound (273 mg). δ (d$^6$-DMSO) 1.59–1.86 (m, 3H), 2.16–2.31 (m, 1H), 2.35–2.46 (m, 1H), 2.95–3.09 (m, 1H), 3.53–3.82 (m, 2H), 3.66 (s, 3H), 4.78 (s, 1H), 7.12 (d, 1H, J=9.5 Hz), 7.47 (d, 2H, J=8 Hz), 7.64–7.76 (m, 4H), 7.84 (s, 1H), 9.93 (s, 1H).

INTERMEDIATE 61 cis-5-[2-Methoxy-5-(5-methyl-tetrazol-1-yl)-benzylamino]6-(4-triflyoromethylphenyl)-piperidin-2-one From cis-5-amino-6-(4-trifluoromethyl-phenyl)-piperidin-2-one (207 mg) and 2-methoxy-5-(5-methyl-

29 tetrazol-1-yl)-benzaldehyde (155 mg) to give the title compound (217 mg). Mass spectrometry. For $C_{22}H_{23}F_3N_6O_2$, m/z 461 (MH$^+$).

INTERMEDIATE 62

4-(5-phenyl-tetrazol-1-yl)-phenol

To a suspension of acetic acid 4-benzolylamino-phenyl ester (10.28 g) in acetonitrile (200 ml) at 0° sodium azide (2.62 g) was added. Trifluoroacetic anhydride (6.8 ml) was then added dropwise under an atmosphere of nitrogen. After stirring at room temperature for 18 h, aqueous ammonia (35% solution, 200 ml) was added and the mixture stirred for 16 h. The mixture was then extracted with dichloromethane (3×150 ml), the organic layers combined, dried (Na$_2$SO$_4$), and evaporated in vacuo. The residues were purified by column chromatography eluting with 10% ethyl acetate in dichloromethane to yield the title compound as a solid (2.5 g). T.l.c. (5% Ethyl acetate/dichloromethane), Rf 0.28.

INTERMEDIATE 63

N-[1-(3-Formyl-4-methoxy-phenyl)-1H-tetrazol-5-yl]-acetamide

To a suspension of 1-(3-[1,3]dioxolan-2-yl-4-methoxy-phenol)-1H-tetrazol-5-ylamine (0.5 g) in dichloromethane (5 ml), triethylamine (0.53 ml), acetic anhydride (0.18 ml) and dimethylaminopyridine (10 mg) were sequentially added. The mixture was stirred under an atmosphere of nitrogen for 2 h. Pyridine (1 ml) was then added and the mixture stirred for 18 h. The solvents were then evaporated to dryness and the residue dissolved in tetrahydrofuran (10 ml). Aqueous hydrogen chloride solution (10 ml, 2N) was then added and the mixture stirred for 30 min. The mixture was then diluted with dichloromethane (50 ml) and brine added (20 ml). The phases were separated and the aqueous layer extracted with dichloromethane (2×50 ml). The organic layers were combined, dried (Na$_2$SO$_4$), and evaporated in vacuo and the residue was purified by column chromatography eluting with ethyl acetate/dichloromethane mixtures and the main product collected. The material was crystallized by trituration in ether to give the title compound as a yellow solid (155 mg). T.l.c. (5% Methanol/dichloromethane) Rf 0.3.

INTERMEDIATE 64

1-(3-[(1,3]Dioxolan-2-yl-4-methoxy-phenyl)-1H-tetrazole

To a suspension of 2-methyoxy-5-tetrazol-1-yl-benzaldehyde (8 g) in toluene (400 ml), ethylene glycol (8 ml) and para-toluene sulphonic acid (50 mg) were added. The mixture was heated to reflux under Dean-Stark conditions and under a nitrogen atmosphere for 12 h whereupon evolution of water had ceased. The mixture was allowed to cool and the liquor decanted and extracted with 8% aqueous sodium bicarbonate solution (100 ml). The precipitated solid was dissolved in dichloromethane (200 ml) and then extracted with the aqueous layer. The aqueous layer was then extracted with dichloromethane (100 ml). The organic layers were then combined, dried (Na$_2$SO$_4$) and evaporated in vacuo to yield the title compound as a yellow solid (9.12 g). T.l.c. (5% Methanol/methyl tert-butyl ether), Rf 0.5.

Similarly prepared:

INTERMEDIATE 65

1-(3-[1,3]Dioxolan-2-yl-4-methoxy-phenyl)-5-methyl-1H-tetrazole

From 2-methoxy-5-(5-methyl-tetrazol-1-yl)-benzaldehyde (400 mg) and ethylene glycol (0.32 ml) to give the title compound (500 mg) as a pale orange solid, m.p. 103°.

30

INTERMEDIATE 66

1-(3-[1,3]Dioxolan-2-yl-4-methoxy-phenyl)-5-methylsulfanyl-1H-tetrazole

From 2-methoxy-5-(5-methylsulfanyl-tetrazol-1-yl)-benzaldehyde (2.1 g) and ethylene glycol (9.3 ml) to give the title compound as an off-white solid (2.3 g). T.l.c. (Ethyl acetate/cyclohexane (1:1)), Rf=0.8

INTERMEDIATE 67

(2-[1,3]Dioxolan-2-yl-4-methoxy-phenyl)-cyanamide

To a solution of 1-(3-[1,3]dioxolan-2-yl-4-methoxy-phenyl)-1H-tetrazole (9.09 g) in dry tetrahydrofuran (200 ml) at −78° under nitrogen, n-butyl lithium solution in hexane (30 ml of 1.6 mol dm$^{-3}$) was added. Nitrogen gas was evolved. After stirring under nitrogen for 5 min the mixture was allowed to warm to 0° over 10 min and 8% aqueous sodium bicarbonate (200 ml) was then added. After stirring for 10 min ethyl acetate (150 ml) was added and the layers separated. The aqueous layer was then extracted with dichloromethene (2×200 ml) and the organic layers combined, dried (Na$_2$SO$_4$) and evaporated in vacuo to yield the title compound as an oil (8.0 g). T.l.c. (5% Methanol/methyl tert-butyl ether), Rf 0.7.

INTERMEDIATE 68

1-(3-[1,3]Dioxolan-2-yl-4-methoxy-phenyl)-1H-tetrazol-5-ylamine

To a solution of (2-[1,3]dioxolan-2-yl-4-methoxy-phenyl)-cyanamide (7.82 g) in dimethylformamide (150 ml) ammonium chloride (22.8 g) and sodium azide (18.5 g) were added and the mixture heated to 80° under a nitrogen atmosphere. After 2½h the mixture was cooled and brine (250 ml) and water (100 ml) were added. The mixture was extracted with dichloromethane (3×250 ml and 1×100 ml). The organic layers were combined, dried (Na$_2$SO$_4$), and evaporated in vacuo. The resulting solid residue was washed with ether (100 ml) and dried in vacuo to yield the title compound as a light yellow solid (7.2 g). T.l.c. (5% Methanol/methyl tert-butyl ether), Rf 0.13.

INTERMEDIATE 69

5-(5-Dimethylamino-tetrazol-1-yl)-2-methoxy-benzaldehyde

To a suspension of 1-(3-[1,3]dioxolan-2-yl-4-methoxy-phenyl)-1H-tetrazol-5- ylamine (500 mg) in dry tetrahydrofuran (5 ml) sodium hexamethyl disilazide solution (2 ml of 1.0M in tetrahydrofuran) was added at room temperature under nitrogen. The mixture was stirred for 5 min before addition of methyl iodide (0.15 ml). The mixture was stirred for 10 min before addition of more sodium hexamethyl disilazide solution (2 ml; 1.0M in tetrahydrofuran). The mixture was stirred for 5 min before addition of more methyl iodide (0.15 ml). The mixture was stirred for 18 h then aqueous hydrogen chloride solution (10 ml; 2M) was added and the mixture stirred for 30 min. Brine (20 ml) and dichloromethane (50 ml) were added and the layers separated. The aqueous layer was extracted with dichloromethane (2×50 ml) and the organic layers combined, dried (Na$_2$SO$_4$) and evaporated in vacuo. The resulting residue was purified by column chromatography eluting with 10% ethyl acetate in dichloromethane to give the title compound as a yellow solid (230 mg). T.l.c. (5% Methanol/ dichloromethane), Rf 0.45.

Similarly prepared:

INTERMEDIATE 70

5-(5-Diethylamino-tetrazol-1-yl)-2-methoxy-benzaldehyde

From 1-(3-[1,3]dioxolan-2-yl-4-methoxy-phenyl)-1H-tetrazol-5-ylamine (0.5 g) and ethyl iodide (0.32 ml in two portions) to give the title compound as a yellow solid (0.224 g). T.l.c. (5% Methanol/dichloromethane), Rf 0.5.

INTERMEDIATE 71

(3-Formyl-4-methoxy-phenyl)-cyanamide

To a solution of 1-(3-[1,3]-dioxolan-2-yl-4-methoxy-phenyl)-1H-tetrazole (0.46 g) in tetrahydrofuran (10 ml) at 0° under nitrogen n-butyl lithium (1.7 ml; a 1.6M solution in hexane) was added. After stirring for 5 min dilute aqueous hydrogen chloride solution (5 ml) and acetone (2 ml) were added. The mixture was stirred for 1 h before addition of dichloromethane (30 ml) and 8% aqueous sodium bicarbonate solution (20 ml). The layers were separated and the aqueous layer extracted with dichloromethane (3×30 ml). The organic layers ware combined, dried (Na$_2$SO$_4$), and evaporated to leave an orange solid. The material was washed with a small amount of ether and cyclohexane and dried in vacuo to yield the title compound as an orange solid (0.31 g). T.l.c.(5% Methanol/methyl tert-butyl ether), Rf 0.6.

INTERMEDIATE 72

2-Methoxy-5-[5-(3,3,3-trifluoro-2-oxo-propyl)-tetrazol-1-yl]-benzaldehyde n-Butyl lithium in hexane (0.25 ml; 1.6M) was added to a solution of 1-(3-[1,3]dioxalan-2-yl-4-methoxy-phenyl)-5-methyl-1H-tetrazole (100 mg) in tetrahydrofuran (5 ml) at −78°. After 10 min trifluoroacetic anhydride (0.064 ml) was added and the reaction was stirred under nitrogen at room temperature for 72 h. 8% Aqueous sodium hydrogen carbonate (20 ml) was added and the product was extracted in dichloromethane (3×20 ml). The combined organic parts were concentrated in vacuo to give a yellow oil. A solution of this oil in acetone (3 ml) and 2N hydrochloric acid (3 ml) was stirred at room temperature for 2 h. The acetone was removed in vacuo and the product was extracted with dichloromethane (3×20 ml). The combined organic parts were dried over sodium sulfate and concentrated in vacuo to give a yellow gum. Purification by chromatography with methanol:methyl t-butyl ether (2.5:97.5) as eluant to afford the title compound (50 mg) as a pale yellow solid, m.p. 128°.

INTERMEDIATE 73

1-(3-[1,3]Dioxolan-2-yl4-methoxy-phenyl)-5-methyanesulfonyl-1H-tetrazole m-Chloroperbenzoic acid (MCPBA) (1.2 g) was added to a solution of 1-(3-[1,3]dioxolan-2-yl-4-methoxy-phenyl)-5-methylsulfanyl-1H-tetrazole (800 mg) in chloroform (15 ml) at room temperature under nitrogen. After 3 h a further quantity of MCPBA (1.2 g) was added and left to stir for 24 h. The mixture was poured into aqueous sodium sulphite (200 ml) and stirred for 30 min. This was then extracted with chloroform (3×60 ml), dried (Na$_2$S$_4$O) and evaporated to give the title compound as a yellow oil (800 mg). T.l.c. (Ethyl acetate/cyclohexane (1:1)), Rf=0.5

INTERMEDIATE 74

5-(5-Methanesulfonyl-tetrazol-1-yl)-2-methoxy-benzaldehyde 1-(3-[1,3]Dioxolan-2-yl-4-methoxy-phenyl)-5-methanesulfonyl-1H-tetrazole (800 mg) in tetrahydrofuran (13 ml) and hydrochloric acid (2N, 7.5 ml) was stirred at room temperature for 1.5 h. The solution was basified with sodium bicarbonate solution (8%), saturated with brine (50 ml), extracted with ether (3×50 ml), dried (N$_2$SO$_4$) and evaporated to give the title compound as an orange solid (307 mg). T.l.c. (Ethyl acetate/cyclohexane (1:1)), Rf=0.5

INTERMEDIATE 75

1-(4-Benzyloxy-3-fluoro-phenyl)-5-methyl-1H-tetrazole

4-Benzyloxy-3-fluoro-phenylamine as a solution in acetic acid (50 ml) was heated to 75° under nitrogen. Triethylorthoacetate (10.3 ml) was added. After a further 45 min at this temperature, sodium azide (7.8 g) was added portionwise. Heating was continued for a further 3 h, the reaction cooled overnight and poured into sodium bicarbonate solution (8%, ca. 500 ml), extracted with dichloromethane (3×100 ml), dried (Na$_2$SO$_4$) and evaporated. The residue was purified by FCC with (dichloromethane/methanol (995:5)) to give the title compound as a solid (4.6 g). T.l.c. (Dichloromethane/methanol (995:5)), Rf 0.45.

INTERMEDIATE 76

2-Fluoro-4-(5-methyl-tetrazol-1-yl)-phenol

A suspension of 1-(4-benzyloxy-3-fluoro-phenyl)-5-methyl-1H-tetrazole (4.6 g) in ethanol (300 ml) was hydrogenated at room temperature and pressure over a pre-reduced suspension of palladium-on-carbon (10% paste, 1.4 g) until uptake ceased. The catalyst was filtered off and the filtrate evaporated to give the title compound as a cream solid (3.6 g). T.l.c. (Dichloromethane/methanol (995:5)), Rf 0.45.

INTERMEDIATE 77

Cyclopropanecarboxylic acid (4-benzyloxy-phenyl)-amide

Cyclopropane carbonyl chloride (4.54 ml) was added dropwise over 5 min to a stirred solution of 4-benzyloxyaniline hydrochloride (11.8 g) and triethylamine (15.33 ml) in dichloromethane (60 ml). The reaction mixture was stirred at room temperature under nitrogen for 2 h. The solution was diluted with 2N hydrochloric acid (100 ml) and dichloromethane (200 ml). The organic layer was washed with 2N sodium carbonate (100 ml), water (100 ml), 10% brine (50 ml) and dried over anhydrous sodium sulphate. Concentration in vacuo gave a pale brown solid which was washed with diethyl ether (3×50 ml) to afford the title compound (12 g) as a white solid, m.p. 162°.

INTERMEDIATE 78

1-(4-Benzyloxy-phenyl)-5-cyclopropyl-1H-tetrazole

Trifluoromethane sulfonic anhydride (9.42 ml) was added dropwise over 10 min to a solution of cyclopropanecarboxylic acid(4-benzyloxy-phenyl)-amide (15 g) and sodium azide (3.64 g) in acetonitrile (250 ml) at 0°. The reaction mixture was stirred at room temperature under nitrogen for 16 h. 10% Aqueous sodium hydrogen carbonate (80 ml) was added and the organic layer was separated. The aqueous layer was further extracted with ethyl acetate (2×100 ml). The combined organic pads were dried over anhydrous sodium sulphate and concentrated in vacuo to give a brown oil. Purification by chromatography with ethyl acetate:isohexane (1:1) as eluant afforded the title compound (2.4 g) as a yellow solid, m.p. 118°.

INTERMEDIATE 79

4-(5-Cyclopropyl-tetrazol-1-yl)-phenol

A solution of 1-(4-benzyloxy-phenyl)-5-cyclopropyl-1H-tetrazole (2.3 g) in ethanol (75 ml) was added to a suspension of 10% palladium on charcoal catalyst (400 mg) in ethanol (10 ml) and the mixture was stirred under a hydrogen atmosphere for 1 h. The catalyst was removed by filtration and the solution concentrated in vacuo to afford the title compound (1.57 g) as a pale yellow solid, m.p. 184°.

Similarly prepared:

INTERMEDIATE 80

4-Tetrazol-2-yl-phenylamine

From 2-(4-nitro-phenyl)-2H-tetrazole (7.3 g) to give the title compound as a beige solid (5.4 g). T.l.c. (Cyclohexane/ Ethyl acetate (3:1)), Rf 0.65.

INTERMEDIATE 81

4-(5-Methylsulfanyl-tetrazol-1-yl)-phenol

A solution of sodium hydroxide (2.06 g) in water (120 ml) followed by methyl iodide (3.5 ml) was added to a solution of 1-(4-hydroxyphenyl)-1H-tetrazole-5-thiol (10 g) in tetrahydrofuran (30 ml) and stirred at room temperature for 5 h. The mixture was poured into brine (120 ml), extracted with ethyl acetate (3×60 ml), dried ($Na_2SO_4$) and evaporated to give the title compound as a brown solid (10.64 g). T.l.c. (Dichloromethane/methanol (990:10)), Rf=0.42

INTERMEDIATE 82

3-Nitro-2-p-tolyl-pyridine

A stirred mixture of 2-chloro-3-nitropyridine (10.6 g), p-tolylboronic acid (19.69 g) and tetrakis (triphenylphosphine)palladium (O) (0.16 g) in 2N sodium carbonate solution (100 ml) and dimethoxyethane (100 ml) was heated to reflux under nitrogen. After 64 h the mixture was cooled then filtered through hyflo eluting with more dimethoxyethane. The filtrate was evaporated in vacuo to give an oil which was redissolved with ether (300 ml) and washed with 5N sodium hydroxide solution (300 ml). The aqueous portion was further extracted with ether (300 ml×2). The combined organic extracts ware washed with water (200 ml), 1N hydrochloric acid (2×100 ml) and saturated brine. were dried ($MgSO_4$) and evaporated in vacuo. The resultant crystalline solid was triturated with hexane to give the title compound as a yellow crystalline solid (11.66 g). T.l.c. (Hexanelethylacetate (2:1)), Rf 0.52, Similarly prepared:

INTERMEDIATE 83

5-(1-Ethyl-1H-tetrazol-5-yl)-2-methoxy-benzaldehyde

From 5-bromo-1-ethyl-1H-tetrazole (620 mg) and 3-formyl-4-methoxy-phenylboronic acid (0.69 g) to give the title compound (483 mg) as a white solid. T.l.c. (Ether) Rf 0.2.

INTERMEDIATE 84

5-(1-Cyclopropylmethyl-1H-tetrazol-5-yl)-2-methoxy-benzaldehyde

From a mixture of 5-bromo-1-cyclopropylmethyl-1H-tetrazole with 5-bromo-2-cyclopropyl-2H-tetrazole (1.91 g) and 3-formyl-4-methoxy-phenyl-boronic acid (1.86 g) to give the title compound (657 mg) as a yellow solid. NMR ($CDCl_3$) δ 0.45 (2H,m); 0.70 (2H,m); 1.3 (1H,m); 4.05 (3H,s); 4.3(2H,d); 7.2 (1H,d); 8.0 (1H,m); 8.15 (1H,d); 10.55 (1H,s).

INTERMEDIATE 85 cis-2-p-Tolyl-piperidin-3-ylamine

A stirred solution of 3-nitro-,2-p-tolyl-pyridine (5.0 g) in ethanol (200 ml) and concentrated. hydrochloric acid (15 ml) was hydrogenated over pre-reduced platinum oxide (1.5 g) at 23° 1 atm until hydrogen uptake was complete (~3 lh). The mixture was filtered through hyflo washing the pad of hyflo with water then the filtrate was evaporated in vacuo. Recrystallisation from isopropanol water gave a cream solid. The solid was treated with 2N sodium hydroxide solution and extracted with dichloromethane (5×200 ml). The combined organic extracts were dried ($Na_2SO_4$) and evaporated in vacuo to give the title compound as an orange-brown oil which partially crystallised on standing (2.20 g). T.l.c. (Dichloromethane/ethanol/ammonia (100:8:1) Rf 0.43.

INTERMEDIATE 86

(4-Benzyloxy-phenyl)-(1-chloro-2,2,2-trifluoro-ethylidene)-amine

A mixture of resin-supported triphenylphosphine (3 mmol triphenylphosphine/g resin; 58.6 g) and N-(4-benzyloxy-phenyl)-2,2,2-trifluoro-acetamide in carbon tetrachloride (800 ml) was heated to reflux under nitrogen for 18 h. The mixture was allowed to cool then filtered, washing the resin with dichloromethane (1l) and ether (1l). The organics were concentrated in vacuo to give the title compound as a yellow solid (20.7 g). T.l.c. (Cyclohexanelethyl acetate (9:1)) Rf 0.81

INTERMEDIATE 87

1-(4-Benzyloxy-phenyl)-5-trifluoromethyl-1H-tetrazole (4-Benzyloxy-phenyl)-(1-chloro-2,2,2-trifluoro-ethylidene)-amine (66 mmol) was added to a stirred flask of glacial acetic acid (250 ml) at 70° under nitrogen. After 4 min sodium azide (210 ml) was added and heating was continued for 3 h. After cooling the mixture was filtered, the filtrate poured into water (750 ml) then extracted with dichloromethane (500 ml×3). The combined organic extracts were dried ($Na_2SO_4$) and evaporated in vacuo. Purification by FCC using hexane-ethyl acetate (19:1) gave the title compound as a white solid (14.5 g). T.l.c. (Cyclohexane/ethyl acetate (19:1) Rf 0.22

INTERMEDIATE 88

4-(5-Trifluoromethyl-tetrazol-1-yl)-phenol

A solution of 1-(4-benzyloxy-phenyl)-5-trifluoromethyl-1H-tetrazole (45.3 mmol) in ethanol (100 ml) and tetrahydrofuran (100 ml) was hydrogenated at room temperature and atmospheric pressure over 10% palladium-carbon catalyst (6 g). After 2 h, the mixture was filtered and the filtrate was evaporated to give the title compound (10.4 g) as a cream solid. T.l.c. (Dichlormethane/ethanol/ammonia (200:8:1)) Rf 0.3.

INTERMEDIATE 89

2-Methoxy-5-tetrazol-2-ylmethyl-benzaldehyde (A) and 2-Methoxy-5-tetrazol-1-ylmethyl-benzaldehyde (B).

A mixture of 5-Bromomethyl-2-methoxy-benzaldehyde with 5-chloromethyl-2-methoxy-benzaldehyde (0.5 g), tetrazole (306 mg) and triethylamine (608 μl) in dichloromethane (10 ml) was stirred at room temperature for 48 h. The mixture was washed with hydrochloric acid (20 ml;2N) then sodium carbonate solution (20 ml;2N), dried (MgSO$_4$) and the solvent removed to leave the crude product (373 mg). This was purified by column chromatography, eluting with ether to give the title compound (A) (103 mg), T.l.c. (ether) Rf 0.37 and the title compound (B) (170 mg), T.l.c. (ether) Rf 0.05.

INTERMEDIATE 90

2-(4-Nitro-phenyl)-2H -tetrazole

A mixture of 1-fluoro-4-nitrobenzene (20 g), potassium carbonate (23.5 g) and 1H-tetrazole (12 g) in dimethylformamide (60 ml) was heated to 100° under nitrogen for 24 h. On cooling, the solvent was evaporated and the residue taken up in water, extracted with dichloromethane (4×100 ml), dried (Na$_2$SO$_4$) and evaporated to give an orange solid. This was purified by FCC (cyclohexane/ethyl acetate (3:1)) to give the title compound as a solid (6.5 g). T.l.c. (Cyclohexane/ethyl acetate (3:10), Rf 0.43.

INTERMEDIATE 91

4-Tetrazol-2-yl-phenol

A suspension of 4-tetrazol-2-yl-phenylamine (5.4 g) in water (42 ml) and conc sulphuric acid (10 ml) was added slowly to a solution of sodium nitrite (2.3 g) in water (8.5 ml) at 5°. The resulting green solution was stirred at this temperature for ca. 30 min, treated with a mixture of water (50 ml) and conc. sulphuric acid (67 ml) and heated to 120° for 1 h. Water (170 ml) was added, the reaction mixture cooled, saturated with brine (100 ml) and extracted with dichloromethane (3×100 ml), dried (Na$_2$SO$_4$) and evaporated to give the title compound as an orange solid (1.6 g). T.l.c. (Ethyl acetate/cyclohexane (1:1)), Rf 0.55.

INTERMEDIATE 92

2-Hydroxy-5-tetrazol-2-yl-benzaldehyde

Hexamethylenetetramine (5.6 g) was added to 4-tetrazol-2-yl-phenol (1.6 g) in trifluoroacetic acid (40 ml) and the mixture heated at 60° for 24 h. On cooling, the solution was poured into sulphuric acid (2N, 100 ml), extracted with ether (3×100 ml), dried (Na$_2$SO$_4$) and evaporated. The residue was purified by FCC (dichloromethane) to give the title compound as a yellow solid (930 mg). T.l.c. (Dichloromethane), Rf 0.56.

INTERMEDIATE 93

2-Methoxy-5-tetrazol-2-yl-benzaldehyde

Potassium carbonate (1.06 g) and methyl iodide (0.5 ml) were added to a solution of 2-hydroxy-5-tetrazol-2-yl-benzaldehyde (930 mg) in dimethylformamide (6 ml) at room temperature. The mixture was stirred for 2 h then evaporated to give an orange solid. This was dissolved in water (40 ml), extracted with dichloromethane (3×30 ml), dried (Na$_2$SO$_4$) and evaporated. The residue was purified by FCC (dichloromethane) to give the title compound as a yellow solid (423 mg). T.l.c. (Ethyl acetate/cyclohexane (1:1)), Rf 0.44.

INTERMEDIATE 94

2-Methoxy-5-(1H-tetrazol-5-yl)-benzaldehyde

Tributyltinazide (1.7 g) was added to 3-[1,3]dioxolan-2-yl-4-methoxy-benzonitrile (500 mg) followed by a further two portions (2×1.7 g) of tributyltinazide. The mixture was stirred at 160° for 2 h. After cooling the thick oil was partitioned between 2N sodium hydroxide solution (30 ml) and ether (3×30 ml). The aqueous phase was acidified with concentrated hydrochloric acid and the mixture extracted into ethyl acetate (3×70 ml). The ethyl acetate fractions were dried (MgSO$_4$) and concentrated to afford the title compound as a pale yellow solid (530 mg). (δ, CDCl$_3$) 4.04 (3H,s), 7.18 (1H,d), 8.43 (1H,dd), 8.57 (1H,d), 10.53 (1H, s)

INTERMEDIATE 95

2-Methoxy-5-(1-methyl-1H-tetrazol-5-yl)-benzaldehyde (A) and 2-Methoxy-5-(2-methyl-2H-tetrazol-5-yl)-benzaldehyde (B)

A mixture of potassium carbonate (400 mg) and 2-methoxy-5-(1H-tetrazol-5-yl)-benzaldehyde (400 mg) in dimethylformamide (10 ml) was stirred for ½ hour then iodomethane (0.18 ml) was added and stirring continued for 20 h. Water (20 ml) was added and the mixture extracted with ethyl acetate (3×20 ml). The organics were dried (MgSO$_4$) and concentrated in vacuo to afford a yellow solid (370 mg). The solid was purified by FCC eluting with Petrol/ether (1:1→0:1) to afford the title compound (B) (320 mg).T.l.c. (Dichloromethane/ethanol/ammonia(200:8:1)) Rf 0.62 and the title compound (A) T.l.c. (Dichloromethane/ethanol/ammonia(200:8:1)) Rf 0.37.

INTERMEDIATE 96

1-Cyloropropylmethyl-1H-tetrazole and 2-cyclopropylmethyl-2H-tetrazole

A mixture of cyclopropylmethylbromide (15 g), tetrazole (12 g), triethylamine (23.8 ml) and 4-dimethylaminopyridine (25 mg) in dichloromethane (500 ml) was left to stand overnight at room temperature. The mixture was washed with water (250 ml) and 2N aqueous sodium carbonate (2×250 ml), dried (MgSO$_4$) and concentrated in vacuo to afford the title compounds as ca (1:1) mixture (8.0 g).

INTERMEDIATE 97

5-Bromo-1-cyclopropylmethyl-1H-tetrazole and 5-bromo-2-cyclopropyl-2H-tetrazole.

A solution of bromine (21.5 g) in chloroform (20 ml) was added dropwise to a solution of 1-cyclopropylmethyl-1H-tetrazole and 2-cyclopropylmethyl-2H-tetrazole (8.0 g) in acetic acid (50 ml) and chloroform (100 ml) at reflux under nitrogen. After heating for 18 h the mixture was cooled and evaporated in vacuo to give a red oil. This was dissolved in ethyl acetate (200 ml) and washed with aqueous sodium metabisulphite solution, water (100 ml) then saturated brine, dried (MgSO$_4$) and evaproated in vacuo. Trituration with ether gave the title compound (1.91 g) as a grey solid. T.l.c. (Hexane/ethylacetate(9:1)) Rf 0.87. Evaporation of the triturate gave a second portion of the title compound as a black oil (7.52 g).

INTERMEDIATE 98

2-Methoxy-5-(tetrazol-1-yl) benzoic acid, methyl ester

Sodium azide (0.54 g) was added to a stirred solution of 2-methoxy-5-amino benzoic acid, methyl ester (1 g) and triethyl orthoformate (1.38 ml) in glacial acetic acid (8 ml) and dimethylformamide (2 ml). The mixture was heated to 79°–80°. After 1¼h, the solution was allowed to cool (ice-water bath) and a solution of sodium nitrite (0.57 g) in water (10 ml) was added slowly. After stirring for 30 min, water (40 ml) was added. After 2 h, the mixture was filtered. The residual white solid was washed with water and dried in vacuo, at 25° to give the title compound (0.83 g); mp 185°–187°.

INTERMEDIATE 99

2-Methoxy-5-(tetrazol-1-yl)phenylmethanol

Lithium borohydride (196 mg) was added to a stirred and cooled (ice-water bath) suspension, under nitrogen, of 2-methoxy-5-(tetrazol-1-yl) benzoic acid, methyl ester (1 g) in tetrahydrofuran (15 ml). After 2 min a solution of methanol (288 mg) in tetrahydrofuran (2 ml) was added over 1 min. The cooling bath was removed and the mixture stirred for 86 min. The solution was cooled (ice-water bath) and 3M aqueous hydrochloric acid (½–1 ml) was added, forming a thick gel. Water (5 ml) was added, followed by more 3M aqueous hydrochloric acid (5 ml). A solution of sodium nitrite (325 mg) in water (1 ml) was then added. After 1¼ h, water (15 ml) was added and the resulting solution was extracted with ethyl acetate. The organic phase was washed successively with dilute hydrochloric acid and water, and then dried (MgSO$_4$). Evaporation gave a yellow solid which was stirred with ethyl acetate (ca 3 ml). Filtration gave a grey/white solid, which was washed with a mixture of ethyl acetate and petroleum ether (bp 60°–80°) (1:1) and dried to give the .title compound (331 mg); nmr, δ (d$^6$-DMSO), 3.88 (s,3H), 4.58 (d,2H, J=ca 8 Hz), 5.34 (t, 1H, J=ca 8 Hz), 7.20 (d, 1H, J=ca 10 Hz), 7.75 (dd, 1H, J=ca 10 Hz, J=ca 4 Hz), 7.86 (d, 1H, J=ca 4 Hz), 10.01 (s, 1H).

INTERMEDIATE 100

2-Methoxy-5-(tetrazol-1-yl)benzaldehyde

Active manganese dioxide (77 mg) was added to a stirred solution of 2-methoxy-5-(tetrazol-1-yl)phenylmethanol (40 mg) in tetrahydrofuran (1 ml). After 30 min the mixture was heated in an oil-bath at 70°. After a further 30 min, active manganese dioxide (67 mg) was added. After a further 1 h the mixture was allowed to cool and then filtered. The filtrate was evaporated to give the title compound as a yellow solid (33 mg); nmr, δ (d$^6$-DMSO), 4.4 (s,3H), 7.53 (d, 1H, J=ca 10 Hz), 8.12–8.23 (m, 2H), 10.12 (s, 1H), 10.40 (s, 1H).

EXAMPLE 1

(2-Methoxy-5-tetrazol-1-yl-benzyl)-(cis-2-phenyl-piperidin-3-yl)-amine dihydrochloride To a solution of cis-2-phenylpiperidin-3-yl-amine (1.22 mmol) and 2-methoxy-5-tetrazol-1-yl-benzaldehyde (1.22 mmol) in dichloromethane (25 ml) was added sodium triacetoxy borohydride (1.7 mmol) and 2 drops of glacial acetic acid. The mixture was stirred at room temperature under nitrogen atmosphere for 18 h. The solvent was evaporated in vacuo and the residue quenched with 2N solution of sodium carbonate (20 ml) and extracted with ethyl acetate (3×50 ml). The organic layer was treated with 2N hydrochloric acid solution (20 ml) and the acidic portion basified with 2N sodium carbonate solution and extracted with dichloromethane (3×100 ml). The organic extracts were dried (MgSO$_4$), filtered and concentrated to give a residue which was purified by FCC (dichloromethane/ethanol/ammonia—200:8:1) to give a white foam which was dissolved in ethanol (15 ml) and treated with 1M hydrochloric acid solution in ether (2.5 ml). The solvent was evaporated in vacuo and the resulting white solid triturated with isopropanol and filtered to afford the title compound. (49%). m.p. 242°–243° T.l.c. (Dichloromethane/ethanol/ammonia (200:8:1)) Rf 0.5

Similarly prepared:

EXAMPLE 2

(2-Methoxy-5-tetrazol-1-yl-benzyl)-([2S,3S]-2-phenyl-piperidin-3-yl)-amine dihydrochloride From 2-methoxy-5-(tetrazol-1-yl)-benzaldehyde (0.55 g) and [2S]-phenyl-piperidin-[3S]-yl-amine (0.47 g) to give the title compound as a white solid in 81% yield. m.p. 243°–244° T.l.c. (Dichloromethane/ethanol/ammonia (200:8:1)) Rf 0.5

EXAMPLE 3

[2-Methoxy-5-(5-methyl-tetrazol-1-yl)-benzyl]-(cis-2-phenyl-piperidin-3-yl)-amine dihydrochloride From 2-methoxy-5-(5-methyl-tatrazol-1-yl)-benzaldehyde (1.14 mmol) to give the title compound as a white solid in 60% yield. m.p. 247°–248° T.l.c. (Dichloromethane/ethanol/ammonia (100:8:1)) Rf 0.55

EXAMPLE 4

[5-(5-Ethyl-tetrazol-1-yl)-2-methoxy-benzyl]-(cis-2-phenyl-piperidin-3-yl)-amine dihydrochloride From 5-(5-ethyl-tetrazol-1-yl)-2-methoxy-benzaldehyde (1.07 mmol) to give the title compound in 68% yield as a white solid. m.p. 245°–246°. T.l.c. (Dichloromethane/ethanol/ammonia (200:8:1)) Rf 0.6

EXAMPLE 5

2-methoxy-[5-(5-Propyl-tetrazol-1-yl)-benzyl]-(cis-2-phenyl-piperidin-3-yl)-amine dihydrochloride From 2-methoxy-5-(5-propyl-tetrazol-1-yl)-benzaldehyde (260 mg) to give the title compound as a white solid (343 mg). m.p. 247°–249° T.l.c. (Dichloromethane/ethanol/ammonia, 100:8:1), Rf 0.47.

EXAMPLE 6

[2-Methoxy-5-(5-methyl-tetrazol-1-yl)-benzyl]-([2S,3S]-2-phenyl-piperidin-3-yl) -amine dihydrochloride To a solution of [2S]-phenyl-piperidin-[3S]-ylamine (4.6 mmoles) and 2-methoxy-5-(5-methyl-tetrazol-1-yl)-benzaldehyde (4.6mmoles) in dichloromethane (50 ml) was added sodium triacetoxy borohydride (6.9 mmoles) and 5 drops glacial acetic acid. The mixture was stirred at room temperature under nitrogen atmosphere for 18 h. The solvent was evaporated in vacuo and the residue quenched with 2N solution of sodium carbonate (30 ml) and extracted with ethyl acetate (50 ml). The organic layer was treated with 2N hydrochloric acid (50 ml) and the acidic portion basified with 2N sodium carbonate solution and extracted with dichloromethane (3×100 ml). The organic extracts were dried ($K_2CO_3$), filtered and concentrated to give a residue which was purified by FCC (dichloromethyane/ethanol/ammonia—150:8:1) to give a pale yellow oil which was dissolved in ethanol (50 ml) and treated with 1M hydrochloric acid solution in ether (10 ml). The solvent was evaporated in vacuo to afford the title .compound as a white solid (92%). m.p. 244°–246° T.l.c. (Dichloromethane/ethanol/ammonia (150:8:1)) Rf 0.30

EXAMPLE 7

[2-Methoxy-5-(5-trifluoromethyl-tetrazol-1-yl)-benzyl]-([2S,3S]-2-phenyl-piperidin-3-yl)-amine dihydrochloride A mixture of [2S]-phenyl-piperidin-[3S]-ylamine (1.14 mmol), 2-methoxy-5-(5-trifluoromethyl-tetrazol-1-yl)-benzaldehyde (1.2 mmol), sodium triacetoxyborohydride (2.37 mmol) and acetic acid (3 drops) in dichloromethane (25 ml) was stirred at 23° under nitrogen for 64 h. 2N sodium carbonate solution (50 ml) was added and the mixture extracted with dichloromethane (3×25 ml). The combined extracts ware washed with saturated brine (50 ml), dried ($MgSO_4$) and evaporated. Purification by FCC with dichloromethane/ethanol/ammonia (400:10:1→100:10:1) gave a colourless viscous oil. This was dissolved in methanol (10 ml) and treated with 2N ethereal hydrogen chloride (~10 ml). Evaporation in vacuo and trituration with i-propyl acetate gave the title compound as a white solid (210 mg). T.l.c. (Dichloromethane/ethanol/ammonia (200:10:1)) Rf 0.39 Optical Rotation (c 0.003 g/ml. water) +50.35°.

Similarly prepared:

EXAMPLE 8

[5-(5-Cyclopropyl-tetrazol-1-yl)-2-methoxy-benzyl]-(2S-phenyl-piperidin-3S-yl)-amine dihydrochloride From 2S-phenyl-piperidin-3S-ylamine (176 mg) and 5-(5-cyclopropyl-tetrazol-1-yl)-2-methoxy-benzaldehyde (244 mg) to give the title compound (300 mg) as a pale yellow solid, m.p. 272°. T.l.c. (Dichloromethene/methanol/acetic acid/water (120:15:3:2)), Rf 0.22

EXAMPLE 9

[2-Methoxy-5-(5-methylsulfanyl-tetrazol-1-yl)-benzyl]-(2S-phenyl-piperidin-3S-yl)-amine dihydrochloride From [2S]-phenyl-piperidin-[3S]-ylamine (282 mg) and 2-methoxy-5-(5-methylsulfanyl-tetrazol-1-yl)-benzaldehyde (400 mg) to give the title compound as an off-white solid (484 mg), m.p. 245°. T.l.c. (Dichloromethane/methanol/ammonia (945:50:5)), Rf=0.3

EXAMPLE 10

[2-Methoxy-5-(5-phenyl-tetrazol-1-yl)-benzyl]-(2S-phenyl-piperidin-3S-yl)-amine dihydrochloride From 2-methoxy-5-(5-phenyl-tetrazol-1-yl)-benzaldehyde (0.35 g and 2S-phenyl-piperidin-3S-ylamine (0.218 g), to yield the title compound as a white solid (0.525 g), m.p. 248°–250°. T.l.c. (Dichloromethane/ethanol/ammonia (200:8:1)), Rf 0.25.

EXAMPLE 11

[2 -Methoxy-5-(5-methylimino-4,5-dihydro-tetrazol-1-yl)-benzyl]-(2S-phenyl-piperidin-3S-yl)-amine trihydrochloride From 2-methoxy-5-(5-methylimino-4,5-dihydro-tetrazol-1-yl)-benzaldehyde (117 mg) and 2S-phenyl-piperidin-3S-ylamine (93 mg) to yield the title compound as a white solid (200 mg), m.p. 260°–263° (dec). T.l.c. (Dichloromethane/ethanol/ammonia (100:8:1)), Rf 0.05.

EXAMPLE 12

N-(1 -{4-Methoxy-3-[(2S-phenyl-piperidin-3S-ylamino)-methyl]-phenyl}-1H-tetrazol-5-yl)-acetamide dihydrochloride From [1-(3-formyl-4-methoxy-phenyl)-1H-tetrazol-5-yl]-acetamide (141 mg) and 2S-phenyl-piperidin-3S-ylamine (100 mg) to yield the title compound as a white solid (150 mg), m.p. 228°–230°. T.l.c. (Dichloromethane/ethanol/ammonia (100:8:1)), Rf 0.1.

EXAMPLE 13

[5-(5-Dimethylamino-tetrazol-1-yl)-2-methoxy-benzyl]-(2S-phenyl-piperidin-3S-yl)-amine trihydrochloride From 5-(5-dimethylamino-tetrazol-1-yl)-2-methoxy-benzaldehyde (200 mg) and 2S-phenyl-piperidin-3S-ylamine (150 mg) to yield the title compound as a white solid (307 mg), m.p. 266°–269° (dec.). T.l.c. (Dichloromethane/ethanol/ammonia (100:8:1)), Rf 0.21.

EXAMPLE 14

[5-[5-Diethylamino-tetrazol-1-yl)-2-methoxy-benzyl]-(2S-phenyl-piperidin-3S-yl)-amine trihydrochloride From 5-(5-diethylamino-tetrazol-1-yl)-2-methoxy-benzaldehyde (0.215 g) and 2S-phenyl-piperidin-3S-ylamine (0.137 g) to give the title compound as a white powder (0.34 g), m.p. 229°–231°. T.l.c. (Dichloromethane/ethanol/ammonia (100:8:1)), Rf 0.24.

EXAMPLE 15

1,1,1-Trifluoro-3-(1-{4-methoxy-3-[(2S-phenyl-piperidin-3S-ylamino)-methyl]-phenyl}-1H-tetrazol-5-yl)-propan-2-one dihydrochloride 2S-phenyl-piperidin-3S-ylamine (28 mg) and 2-methoxy-5-[5-(3,3,3-trifluoro-2-oxo-propyl)-tetrazol-1-yl]-benzaldehyde (50 mg) to give the title compound (30 mg) as a white solid, m.p. 284°. T.l.c. (Dichloromethane/ethanol/ammonia (100:8:1)) Rf 0.32

EXAMPLE 16

[5-(5-Methanesulfonyl-tetrazol-1-yl)-2-methoxy-benzyl]-(2S-phenyl-piperidin-3S-yl)-amine dihydrochloride From [2S]-phenyl-piperidine-[3S]-ylamine (125 mg) and 5-(5-methanesulfonyl-tetrazol-1-yl)-2-methoxybenzaldehyde (200 mg) to afford the title compound as a white solid (173 mg), m.p. 235°. T.l.c. (Dichloromethane/methanol/ammonia (967:30:3)), Rf=0.12

EXAMPLE 17

[3-Fluoro-2-methoxy-5-(5-methyl-tetrazol-1-yl)-benzyl]-(2S-phenyl-piperidin-3S-yl)-amine dihydrochloride From [2S]-phenyl-piperidin-[3S]-ylamine (313 mg) and 3-fluoro-2-methoxy-5-(5-methyl-tetrazol-1-yl)-benzaldehyde (755 mg) to afford the title compound as a white solid (275 mg), m.p. 222°. T.l.c. (Dichloromethane/methanol/ammonia (967:30:3), Rf 0.23

EXAMPLE 18 cis-(2-Methoxy-5-tetrazol-1-yl-benzyl)-(2-p-tolyl-piperidin-3-yl)-amine dihydrochloride From cis-2-p-tolyl-piperidin-3-ylamine (0.167 g) and 2-methoxy-5-(5-tetrazol-1-yl)-benzaldehyde (0.180 g) to give the title compound as a white solid (237 mg), m.p. 152°–153°. T.l.c. (Dichloromethane/ethanol/ammonia (200:8:1)) Rf 0.20.

EXAMPLE 19 cis-[2-Methoxy-5-(5-trifluoromethyl-tetrazol-1-yl)-benzyl]-[2-p-tolyl-piperidin-3-yl]-amine dihydrochloride From cis-2-p-tolyl-piperidin-3-ylamine (300 mg) and 2-methoxy-5-(5-trifluoromethyl-tetrazol-1-yl)-benzaldehyde (429 mg) to give the title compound (145 mg) as a pale yellow solid, m.p. 240°. T.l.c. (Dichloromethane/ethanol/ammonia (100:8:1)) Rf 0.35

EXAMPLE 20 cis-[2-Methoxy-5-(5-methyl-tetrazol-1-yl)-benzyl]-(2-p-tolyl-piperidin-3-yl)-amine dihydrochloride From cis-2-p-tolyl-piperidin-3-ylamine (500 mg) and 2-methoxy-5-(5-methyl-tetrazol-1-yl)-benzaldehyde (573 mg) to give the title compound as a white solid (191 mg), m.p. 252°–3°. T.l.c. (Dichloromethane/ethanol/ammonia (95:4:1)), Rf 0.22.

EXAMPLE 21 cis-[2-(3-Bromo-phenyl)-piperidin-3-yl]-(2-methoxy-5-tetrazol-1-yl-benzyl)-amine dihydrochloride From cis-2-(3-bromo-phenyl)-piperidin-3-ylamine (500 mg) and 2-methoxy-5-tetrazol-1-yl-benzaldehyde (403 mg) to give the title compound as a cream solid (145 mg) m.p. 245° dec. T.l.c. (Dichloromethane/ethanol/ammonia (100:8:1)) Rf 0.40.

EXAMPLE 22 cis-[2-Methoxy-5-(5-methyl-tetrazol-1-yl)-benzyl]-[2-(4-methoxy-phenyl)-piperidin-3-yl]-amine dihydrochloride From cis-(4-methoxy-phenyl)-piperidin-3-ylamine (443 mg) [cis-2-(4-Methoxy-phenyl)-piperidin-3-ylamine dihydrochloride (677 mg) was partitioned between dichloromethane (50 ml) and 0.88 ammonia (10 ml). The phases were separated and the aqueous was extracted with dichloromethane (2×30 ml). The combined organics were washed with water (20 ml) and brine (20 ml), dried (Na$_2$SO$_4$) and evaporated in vacuo to leave the free base (443 mg)] and 2-methoxy-5-(5-methyl-tetrazol-1-yl)-benzaldehyde (469 mg) to give the title compound (115 mg) as a white powder with m.p. >145° (darkened), >190° decomposed. T.l.c. (Dichloromethane/ethanol/ammonia, 150:8:1), Rf 0.23.

EXAMPLE 23 cis-[2-(3-Bromo-4-methyl-phenyl)-piperidin-3-yl]-(2-methoxy-5-(5-methyl-tetrazol-1-yl)-benzyl-amine dihydrochloride From 2-methoxy-5-(5-methyl-tetrazol-1-yl)-benzaldehyde (812 mg) and cis-2-(3-bromo-4-methyl-phenyl)-piperidin-3-ylamine (1.03 g) to give the title compound (752 mg) as a white powder with m.p. >220° (decomposed). T.l.c. (Dichloromethane/ethanol/ammonia, 150:8:1) Rf 0.27.

EXAMPLE 24 cis-[2-(3-Chloro-phenyl)-piperidin-3-yl]-(2-methoxy-5-tetrazol-1-yl-benzyl)-amine dihydrochloride From 2-methoxy-5-tetrazol-1-yl-benzaldehyde (300 mg) and cis-2-(3-chloro-phenyl)-piperidin-3-ylamine (423 mg) [cis-2-(3-Chloro-phenyl)-piperidin-3-ylamine dihydrochloride (360 mg) was partitioned between dichloromethane (30 ml) and 0.88 ammonia (10 ml). The phases were separated and the aqueous was washed with dichloromethane (2×20 ml). The combined organics were washed with water (30 ml) and brine (30 ml), dried (Na$_2$SO$_4$) and evaporated in vacuo to leave the free base (260 mg)] to give the title compound (279 mg) as a white powder with m.p. >218° darkened, >245° decomposed. T.l.c. (Dichloromethane/ethanol/ammonia, 150:8:1), Rf 0.24.

EXAMPLE 25

[2S-(4-Fluoro-phenyl)-piperidin-3S-yl]-[2-methoxy-5-(5-trifluoromethyl-tetrazol-1-yl)-benzyl]-amine dihydrochloride From 2S-(4-Fluoro-phenyl)-piperidin-3S-ylamine (300 mg) and 2-methoxy-5-(5-trifluoromethyl-tetrazol-1-yl-benzaldehyde (418 mg), to give the title compound (450 mg) as a pale yellow solid, m.p. 274°. T.l.c. (Dichloromethane/ethanol/ammonia (100:8:1)), Rf 0.57.

EXAMPLE 26 cis-[2-(3-Fluoro-phenyl)-piperidin-3-yl]-[2-methoxy-5-(5-trifluoromethyl-tetrazol-1-yl)-benzyl]-amine dihydrochloride From cis-2-(3-fluoro-phenyl)-piperidin-3ylamine (361 mg) and 2-methoxy-5-(5-trifluoromethyl-tetrazol-1-yl)-benzaldehyde (506 mg) to give the title compound (140 mg) as a pale yellow solid, m.p. 239°. T.l.c. (Dichloromethane/ethanol/ammonia (100:8:1)) Rf 0.51

EXAMPLE 27 cis-[2-(3-Fluoro-4-methylphenyl)-piperidin-3-yl]-[2-methoxy-5-(5-methyltetrazol-1-yl)-benzyl]-amine, dihydrochloride salt From cis-2-(3-fluoro-4-methylphenyl)-3-piperinamine (0.407 g) and 2-methoxy-5-(5-methyltetrazol-1-yl)- benzaldahyde (0.452 g) to give the title compound as a creamy solid (0.603 g). δ (D$_2$O) 2.00–2.40 (m, 3H), 2.28 (s, 3H), 2.43–2.58 (m, 1H), 2.60 (s, 3H), 3.27–3.40 (m, 1H), 3.60–3.74 (m, 1H), 3.75 (s, 3H), 4.00–4.08 (m, 1H), 4.15 (d, 1H, J=13.5 Hz), 4.48 (d, 1H, J=13.5 Hz), 4.95 (d, 1H, J=3.5 Hz), 6.93–7.09 (m, 2H), 7.13 (d, 1H, J=8.5 Hz), 7.36–7.47 (m, 2H), 7.68 (dd, 1H, J=8.5 and 2 Hz). Microanalysis for C$_{22}$H$_{27}$FN$_6$O.2HCl.0.11 H$_2$O, calcd. C, 54.44; H, 6.07; N, 17.31; Cl, 14.61; H$_2$O, 0.4%. Found: C, 53.98; H, 5.98; N, 17.05; Cl, 14:6; H$_2$O, 0.4%.

EXAMPLE 28 cis-[2-(3-Fluorophenyl)-piperidin-3-yl]-[2-methoxy-5-(5-methyltetrazol-1-yl)-benzyl]-amine, dihydrochloride salt From cis-2-(3-Fluorophenyl)-3-piperidinamine (0.390 g) and 2-methoxy-5-(5-methyltetrazol-1-yl)-benzaldehyde (0.46 g) to give the free base (0.6 g) a portion of which (0.376 g) was treated with hydrogen chloride to give the title compound as a white solid (0.409 g). δ (D$_2$O) 2.05–2.4 (m, 3H), 2.45–2.58 (m, 1H), 2.58 (s, 3H), 3.28–3.41 (m, 1H), 3.66–3.74 (m, 1H), 3.78 (s, 3H), 4.01–4.09 (m, 1H), 4.15 (d, 1H, J=13 Hz), 4.45 (d, 1H, J=13 Hz), 5.01 (d, 1H, J=3.5 Hz), 7.07–7.26 (m, 3H), 7.30 (dt, 1H, J=8 and 2 Hz) 7.46 (d, 1H, J=2.5 Hz), 7.52–7.6 (m, 1H), 7.67 (dd, 1H, J=9 and 2.5 Hz). Microanalysis for C$_{21}$H$_{25}$FN$_6$O.2HCl.0.1H$_2$O, calcd. C, 53.52; H, 5.82; N, 17.83; Cl, 15.05; H$_2$O, 0.4%. Found: C, 53.53; H, 5.72; N, 17.85; Cl, 14.9; H$_2$O, 0.4%.

EXAMPLE 29

(2S,3S)-[2-(4-Fluorophenyl)-piperidin-3-yl]-(2-methoxy-5-tetrazol-1-yl-benzyl)-amine, dihydrochloride salt From 2S-(4-fluoro-phenyl)-piperidin-3S-ylamine-2R,3R-bis-(4-methyl-benzyloxy)-succinate (2.14 g) which was dissolved in aqueous ammonia (25 ml concentrated ammonia in 25 ml H$_2$O) and extraction with chloroform (3×40 ml) to give the free base as a clear liquid (0.642 g) and 2-methoxy-5-tetrazol-1-yl-benzaldehyde (710 mg) to give the title compound as a white powdery solid (603.6 mg). δ (D$_2$O), 2.05–2.37 (m, 3H), 2.45–2.59 (m, 1H) 3.26–3.49 (m, 1H), 3.6–3.75 (m, 1H), 3.77 (s, 3H), 3.98–4.07 (m, 1H), 4.17 and 4.41 (2d, 2H, J=12.5 Hz for both), 4.98 (d, 1H, J=2 Hz), 7.22 (q, 3H, J=8 Hz), 7.39 (dd, 2H, J=7.5 and 5 Hz), 7.66 (d, 1H, J=2.5 Hz), 7.85 (dd, 1H, J=8 and 2 Hz). Microanalysis For C$_{20}$H$_{23}$FN$_6$O.2HCl.03H$_2$O, calcd C, 52.14; H, 5.60; N, 18.24; H$_2$O, 1.2%. Found: C: 51.95; H, 5.46; N, 18.09; H$_2$O, 1.2%.

EXAMPLE 30 cis-2-(4-Fluorophenyl)-piperidin-3-yl]-[2-methoxy-5-(methyltetrazol-1-yl)-benzyl]-amine, dihydrochloride salt From cis-2-(4-fluorophenyl)-3-piperidinamine (96 mg) and 2-methoxy-5-(5-methyltetrazol-1-yl)-benzaldehyde (113 mg) to afford the title compound (34 mg). δ (D$_2$O) 2.03–2.35 (m, 3H), 2.42–2.55(m, 1H), 2.58 (s, 3H), 3.25–3.39 (m, 1H), 3.60–3.73 (m, 1H), 3.78 (s, 3H), 3.94–4.03 (m, 1H), 4.13 and 4.39 (2d, 2H, J=13 Hz for both), 4.98 (d, 1H, J=4 Hz), 7.18 (d, 1H, J=9 Hz), 7.27 (t, 2H, J=8.5 Hz), 7.36–7.46 (m, 3H), 7.65 (dd, 1H, J=8.5 and 2.5 Hz). Microanalysis. For C$_{21}$H$_{25}$FN$_6$O.2HCl. 0.7 H$_2$O, calcd. C, 52.33; H, 5.94; N, 17.44; H$_2$O, 2.6%. Found: C, 52.14; H, 5.94; N, 17.28; H$_2$O, 2.6%.

EXAMPLE 31 cis [2-(3,4-Difluorophenyl-piperidin-3-yl]-[2-methyoxy-5-(5methyltetrazol-1-yl)-benzyl]-amine, dihychloride salt From cis-2-(3,4-difluorophenyl)-3-piperidinamine (1.49 g,) and 2-methoxy-5-(5-methyltetrazol-1-yl)-benzaldehyde (218 mg) to give the reductive amination product (187 mg) a portion of which (120 mg) was treated with concentrated hydrochloric acid (3 drops) to give the titled compound (64 mg) δ (D$_2$O) 2.03–2.36 (m, 3H), 2.42–2.58 (m, 1H), 2.58 (s, 3H), 3.26–3.40 (m, 1H), 3.62–3.74 (m, 1H), 3.81 (s, 3H), 3.97–4.06 (m, 1H), 4.15 and 4.42 (2d, 2H, J=13.5 Hz for both), 4.98 (d, 1H, J=3.5 Hz), 7.18–7.52 (m, 5H), 7.68 (dd, 1H, J=9.0 and 2.5 Hz). Microanalysis. For C$_{21}$H$_{24}$F$_2$N$_6$O. 2HCl, calcd. C, 51.75; H, 5.38; N, 17.25%. Found: C, 51.74; H, 5.17; N, 17.31%.

EXAMPLE 32 cis-[2-(3,4-Difluorophenyl)-piperidin-3-yl]-[2-methoxy-5-tetrazol-1-yl-benzyl]-amine, diyhdrochloride salt From cis-2-(3,4-difluorophenyl)-3-piperidinamine (358 mg) and 2-methoxy-5-tetrazol-1-yl-benzaldehyde (360 mg) to give the title compound (529 mg). δ (D$_2$O) 2.05–2.38 (m, 3H), 2.42–2.59 (m, 1H), 3.25–3.39 (m, 1H), 3.62–3.95 (m, 1H), 3.81 (s, 3H), 3.95–4.05 (m, 1H), 4.16 and 4.41 (2d, 2H, J=13 Hz for both), 4.95 (d, 1H), J=3 Hz), 7.13–7.30 (m, 3H), 7.41 (q, 1H, J=8 Hz), 7.69 (d, 1H, J=2 Hz), 7.86 (dd, 1H, J=8 and 2 Hz), 9.59 (s, 1H). Microanalysis. For C$_{20}$H$_{22}$F$_2$N$_6$O.2HCl.0.4H$_2$O, calcd C, 49.99; H, 5.20; N, 17.49; H$_2$O, 1.5%. Found: C, 49.89; H, 5.03; N, 17.38; H$_2$O, 1.5%.

EXAMPLE 33 cis-[2-(3,4-Difluoro-phenyl)-piperidin-3-yl]-[2-methoxy-5-(5-trifluoromethyl-tetrazol-1-yl-benzyl]-amine dihydrochloride From cis-2-(3,4-difluoro-phenyl)-piperidin-3-ylamine (93 mg) and 2-methoxy-5-(5-trifluoromethyl-tetrazol-1-yl)-benzaldehyde (120 mg) to give the title compound (46 mg) as a white solid, m.p. 266°. T.l.c. (Dichloromethane/ethanol/ammonia (100:8:1)), Rf 0.42.

EXAMPLE 34 cis -[2-Methoxy-5-(5-methyl-tetrazol-1-yl)-benzyl]-[2-(4-trifluoromethyl-phenyl)-piperidin-3-yl]-amine, dihydrochloride salt Borane (1M in THF, 2.53 ml) was added to a stirring solution of cis-5-[2-methoxy-5-(5-methyl-tetrazol-1-yl)-benzylamino]-6-(4-trifluoromethyl-phenyl)-piperidin-2-one (193.8 mg) in dry tetrahydrofuran (10 ml). The mixture was stirred at room temperature under nitrogen for 70 h, quenched with saturated aqueous sodium carbonate, extracted with ethyl acetate and dried (MgSO$_4$). Removal of the solvent gave a residue which was treated with trifluoroacetic acid (1 ml) in methanol (25 ml) and heated on a steam bath for 30 mins. Evaporation gave the trifluoroacetic acid salt which was partitioned between aqueous sodium carbonate (2M, 50 ml) and ethyl acetate (50 ml). The organic solution was separated, washed with more aqueous sodium carbonate (2M, 2×50 ml), dried (MgSO$_4$) and concentrated in vacuo to give the crude product (199 mg) which was purified using FCC eluting with 5% methanol-dichloromethane to give the reduction product (115.8 mg). This reduction product (107.3 mg) was dissolved in a mixture of dioxan (0.7 ml) and ethyl acetate (0.3 ml) and concentrated hydrochloric acid (0.26 ml) was added. A white precipitate was formed which was isolated by filtration, washed with ether and dried (98.5 mg). This hydrochloride salt was dissolved in a mixture of methanol (5 ml) and water (0.6 ml) and acetone (20 ml) was added. A solid was formed gradually which was filtered, dried at 40°–45° in vacuo to give the title compound as a creamy white solid (43.9 mg). δ ($D_2O$) 2.08–2.42 (m, 3H), 2.46–2.56 (m, 1H), 2.68 (s, 3H), 3.28–3.43 (m, 1H), 3.72 (s, 3H), 3.70–3.82 (m, 1H), 4.05–4.16 (m, 2H), 4.44 (d, 1H, J=13.5 Hz), 5.07 (d, 1H, J=3 Hz), 7.09 (d, 1H, J=9 Hz), 7.41 (d, 1H, J=2 Hz), 7.49 (d, 2H, J= 8 Hz), 7.64 (dd, 1H, J=9 and 2 Hz) 7.81 (d, 2H, J=8 Hz). Mass spectrometry. For $C_{22}H_{25}F_3N_6O$, m/z 447 (MH$^+$).

Similarly prepared:

EXAMPLE 35 cis-(2-Methoxy-5-tetrazol-1-yl-benzyl)-[2-(4-trifluoromethyl-phenyl)-piperidin-3-yl]-amine, dihydrochloride salt From cis-5-(2-Methoxy-5-tetrazol-1-yl)-benzylamino-6-(4-trifluoromethyl-phenyl)-piperidin-2-one (273.1 mg) and borane (1M in the THF, 3.7 ml) to give the title compound (98.8 mg). δ ($D_2O$) 2.05–2.60 (m, 4H), 3.27–3.44 (m, 1H), 3.67–3.83 (m, 1H), 3.71 (s, 3H), 4.08–4.21 (m, 2H), 4.44 (d, 1H, J=13 Hz), 5.05 (d, 1H, J=3 Hz), 7.09 (d, 1H, J=8.5 Hz), 7.45 (d, 2H, J=8 Hz), 7.66 (d, 1H, J=2Hz), 7.78 (d, 2H, J=8 Hz), 7.83 (dd, 1H, J=8.5 and 2 Hz), 9.59 (s, 1H). Mass spectrometry. For $C_{21}H_{23}F_3N_6O$, m/z 433 (MH$^+$).

EXAMPLE 36

(5-(5-Amino-tetrazol-1-yl)-2-methoxy-benzyl]-(2S-phenyl-piperidin-3S-yl)-amine trihydrochloride To the free base of [4-methoxy-3-(2S-phenyl-piperidin-3S-ylamino-methyl)-phenyl]-cyanamide dihydrochloride (0.08 g) in dimethylformamide (1 ml), sodium azide (0.13 g) and ammonium chloride (0.16 g) were added and the mixture heated to 100° for 18 h under an atmosphere of nitrogen. The mixture was allowed to cool and brine (10 ml) added. The solution was extracted with dichloromethane (3×10 ml) and the organic layers combined, dried ($Na_2SO_4$) and evaporated in vacuo. The residues were purified by column chromatography eluting with dichloromethane:ethanol:ammonia (200:8:1). The isolated product was dissolved in dichloromethane (5 ml) and treated with hydrogen chloride (1 ml of a 1M solution in ether) to give a white precipitate. The solvents were evaporated to give the title compound (0.048 g), m.p. 228–230°. T.l.c. (Dichloromethane/ethanol/ammonia (100:8:1)), Rf0.1.

EXAMPLE 37

(2-Ethoxy-5-tetrazol-1-yl-benzyl)-([2S,3S]-2-phenyl piperidin-3-yl)amine dihydrochloride To a solution of [2S]-phenylpiperidin-[3S]-ylamine (1.9 mmol) in dichloromethane (20 ml), acetic acid (2.7 mmol) was added. Sodium triacetoxyborohydride (2.7 mmol) was then added and the mixture stirred for 2 h and the solvent removed. The residue was partitioned between ethyl acetate (50 ml) and 2N sodium carbonate solution. The aqueous was re-extracted with ethyl acetate (2×50 ml) and the combined organics were dried ($Na_2SO_4$) and reduced to a gum which was dissolved in hot ethanol (10 ml) and treated with concentrated hydrochloric acid. The crystals were harvested and dried to give the title compound (0.68 g) as a white crystalline solid. δ ($D_2O$) 1.32 (3H, t, J=9 Hz), 2.15 (2H, m), 2.35 (1H, m), 2.56 (1H, m), 3.33 (1H, m), 3.74 (1H, m), 4.00 (2H, m), 4.20 (1H, d J=16 Hz), 4.47 (1H, d, J=16 Hz), 4.98 (1H, d, J=4 Hz), 7.12 (1H, d, J=9 Hz), 7.25 (2H, m), 7.45 (3H, m), 7.63 (1H, d, J=3 Hz), 7.82 (1H, dd, J=3, 9 Hz) 9.58 (1H,s) Found: C, 55.51%; H, 6.14%; N, 18.41%; Cl, 15.6%. $C_{21}H_{26}N_6O$.2HCl requires C.55.88%, H, 6.25%; N, 18.26%; Cl, 15.7%

Similarly prepared:

EXAMPLE 38

(2-Isopropoxy-5-tetrazol-1-ylbenzyl)-[(2S,3S]-2-phenyl piperidin-3-yl)amine dihydrochloride From 2-isopropyl-5-tetrazol-1-ylbenzaldehyde (1.29 mmol) to give the title compound (0.44 g) as a white crystalline solid, δ ($D_2O$) 1.30 (6H, m), 2.14 (2H, m), 2.38 (1H, m), 2.55 (1H, m), 3.33 (1H, m), 3.72 (1H, m), 4.02 (1H,m), 4.18 (1H, d J=16 Hz), 4.40 (1H, d, J=16 Hz), 4.63 (1H, m), 4.93 (1H, d J=3 Hz), 7.19 (3H, m), 7.39 (3H, m), 7.60 (1H, d J=3 Hz), 7.82 (1H, dd J=3, 9 Hz), 9.58 (1H, s). Found: C, 55.13%; H, 6.64%; N, 17.47%, Cl, 14.8%. $C_{22}H_{28}N_6O$.2HCl. 0.8$H_2O$ requires C, 55.07%; H, 6.64%; N, 17.51%; Cl, 14.8%.

EXAMPLE 39

(2-Methoxy-5-tetrazol-2-yl-benzyl)-(2S-phenyl-piperidin-3S-yl)-amine dihydrochloride From [2S]-phenyl-piperidin-[3S]-ylamine (173 mg) and 2-methoxy-5-tetrazol-2-yl-benzaldehyde (200 mg) to give the title compound as a white solid (285 mg), m.p. 222°. T.l.c. (Dichloromethane/methyanol/ammonia (945:50:5)), Rf 0.3

EXAMPLE 40

(2-Methoxy-5-tetrazol-1-ylmethyl-benzyl)-(2S-phenyl-piperidin-3S-yl)-amine dihydrochloride From 2S-phenyl-piperidin-3S-ylamine (134 mg) and 2-methoxy-5-tetrazol-1-ylmethyl-benzaldehyde (165 mg) to give the title compound as a white solid (235 mg), T.l.c. (Dichloromethyane/ethanol/ammonia(100:8:1)) Rf 0.29 $[α]_D$=+53.13° (c=0.002 g/ml, $H_2O$).

EXAMPLE 41

(2-Methoxy-5-tetrazol-2-ylmethyl-benzyl)-(2S-phenyl-piperidin-3S-yl)-amine dihydrochloride From 2S-phenyl-piperidin-3S-ylamine (81 mg) and 2-methoxy-5-tetrazol-2-ylmethyl-benzaldehyde (1 00 mg) to give the title compound as a white solid (122 mg), T.l.c. (Dichloromethane/ethanol/ammonia(100:8:1)) Rf 0.36 vmax (KBr) 3412, 2927, 1561, 1510, 1455, 1259, 1029 cm$^{-1}$.

EXAMPLE 42

[2-Methoxy-5-(1-methyl-1H-tetrazol-5-yl)-benzyl]-(cis-2-phenyl-piperidin-3-yl)-amine dihydrochloride From 2-phenyl-piperidin-3-ylamine (81 mg) and 2-methoxy-5-(1-methyl-1H-tetrazol-5-yl)-benzaldehyde (100 mg) to give the title compound (50 mg). T.l.c. (Dichloromethane/ethanol/ammonia(200:8:1)) Rf 0.06 (δ, CDCl₃) 1.45 (1H,dq), 1.59(1H,tt), 1.69 (2H, brs), 1.87 (1H, tt), 2.14(1H,brd), 2.73–2.87 (2H, td and q), 3.26(1H, ddd), 3.53, 3.73 (2H,AB), 3.62 (3H,s), 3.89 (1H,d), 4.0 (3H,s) 6.84 (1H,d), 7.12–7.31(6H,m), 7.56 (1H,dd)

EXAMPLE 43

[2-Methoxy-5-(2-methyl-2H-tetrazol-5-yl)-benzyl]-(cis-2-phenyl-piperidin-3-yl)-amine dihydrochloride From 2-phenyl-piperidin-3-ylamine (240 mg) and 2-methoxy-5-(2-methyl-2H-tetrazol-5-yl)-benzaldehyde (300 mg) to give the title compound (370 mg). T.l.c. (Dichloromethane/ethanol/ammonia(200:8:1)) Rf 0.10 (δ, CDCl₃) 1.41 (1H,dq), 1.61 (1H,tt), 1.91 (1H, tt), 1.69 (2H,brs), 2.16 (1H, brd), 2.8 (1H, td), 2.84 (1H,q), 3.28 (1H, ddd), 3.44, 3.75 (2H, AB), 3.47 (3H,s), 3.88 (1H,d), 4.39 (3H,s), 6.75 (1H,d), 7.16–7.33 (5H,m), 7.81 (1H,d), 7.94 (1H,dd).

EXAMPLE 44

[5-(1-Ethyl-1H-tetrazol-5-yl)-2-methoxy-benzyl]-(2S-phenyl-piperidin-3S-yl)-amine dihydrochloride.

From 5-(1-ethyl-1H-tetrazol-5-yl)-2-methoxy-benzaldehyde (430 mg) and 2S-phenyl-piperidine-3S-ylamine (326 mg) to give the title compound (434 mg) as a white solid, m.p. 273–4°. T.l.c. (Dichloromethane/ethanol/ammonia(100:8:1)) Rf 0.43

EXAMPLE 45

[5-(1-Cyclopropylmethyl-1H-tetrazol-5-yl)-2-methoxy-benzyl]-(2S-phenyl-piperidin-3S-yl)-amine dihydrochloride From 5-(1-Cyclopropylmethyl-1H-tetrazol-5-yl)-2-methoxy-benzaldehyde (300 mg) and 2S-phenyl-piperidin-3S-ylamine (204 mg) to give the title compound (320 mg) as a yellow solid, m.p. 250°–252°. T.l.c. (Dichloromethane/ethanol/ammonia(94:5:1)) Rf 0.34.

Pharmacy Examples

Example A

STERILE FORMULATION

|  |  | mg/ml |
|---|---|---|
| Compound of Example 2 (dihydrochloride) |  | 0.3 mg |
| Sodium Chloride USP |  | 6.0 mg |
| Sodium Acetate USP |  | 2.6 mg |
| Acetic Acid |  | 1.1 mg |
| Water for Injection USP | qs to | 1 ml |

The components are dissolved in a portion of the water for injection and the solution made up to final volume to provide 0.25 mg/ml of the compound of Example 2 as free base.

The solution may be packaged for injection, for example by filling and sealing in ampoules, vials or syringes. The ampoules, vials or syringes may be aseptically filled and/or terminally sterilised by, for example, autoclaving at 121° C.

Further sterile formulations may be prepared, in a similar manner, containing 6 mg of the compound of Example 2 (dihydrochloride) so as to provide 5 mg/ml of the compound of Example 2 as free base.

TABLETS FOR ORAL ADMINISTRATION

Tablets may be prepared by the normal methods such as direct compression or wet granulation.

The tablets may be film coated with suitable film forming materials, such as Opadry White, type YS-1-7027, using standard techniques. Alternatively the tablets may be sugar coated.

Example B

| Direct Compression Tablet |  | mg/Tablet |
|---|---|---|
| Compound of Example 2 (dihydrochloride) |  | 0.6 mg |
| Magnesium Stearate |  | 0.75 mg |
| Avicel PH102 | qs | 150.00 mg |

The compound of Example 2 (dihydrochloride) is passed through a 30 mesh sieve and blended with Avicel PH102 and magnesium stearate. The resultant mix is compressed into tablets using a suitable tablet machine fitted with %₃₂" diameter punches, so as to provide 0.5 mg/tablet of the compound of Example 2 free base.

Tablets of other strengths, containing for example 2.4, 6.0 or 12.0 mg/tablet of the compound of Example 2 (dihydrochloride), may be prepared in a similar manner, so as to provide 2, 5 and 10 mg/tablet of the compound of Example 2 free base.

Example C

WET GRANULATION

A formulation as described in Example B may be used. The compound of Example 2 (dihydrochloride) is dissolved in a suitable volume of granulating solution (purified water or 10% PVP K29/32 in water). After drying, the granules are screened, for example through 20 mesh screen, and blended with magnesium stearate. The granules are then compressed into tablets as described in Example B.

Tablets of other strengths, such as those described in Example B, may be prepared in a similar manner.

Example D

SUPPOSITORY

| Compound of Example 2 (dihydrochloride) |  | 10.0 mg |
|---|---|---|
| Witepsol W32, hard fat | qs | 2000.0 mg |

Blend micronized drug in a portion of the melted Witepsol W32 at approximately 36° C. for approximately 15 minutes in a high speed mixer. Incorporate the homogenized slurry into the remaining portion of the melted Witepsol W32 and blend at approximately 36° C. until satisfactory dispersion is achieved. Fill moulds with 2000 mg formulation, to provide 10 mg/suppository of compound of Example 2 (dihydrochloride).

Example E

CAPSULE

|  | mg/capsule |  |
|---|---|---|
| Compound of Example 2 (dihydrochloride) | 12.0 mg |  |
| Polyethylene glycol | 92.89 mg |  |
| Propylene glycol | qs | 200 mg |

Blend together polyethylene glycol and propylene glycol using heat as necessary. Stir until homogeneous. Add micronised compound of Example 2 (dihydrochloride) to blend. Mix until homogenous. Fill into an appropriate gelatin mass to give soft gelatin capsules containing 200 mg of the formulation, to provide 10 mg/capsule of compound of Example 2 free base. Additional strengths, e.g. 0.5, 2.0 and 5.0 mg/capsule of compound of Example 2 as free base, may be prepared in a similar manner.

Example F

ORAL SYRUP

|  | mg/ml |  |
|---|---|---|
| Compound of Example 2 (dihydrochloride) | 6.0 mg |  |
| Sucrose | 200 mg |  |
| Methylparaben | 1.2 mg |  |
| Propylparaben | 0.15 mg |  |
| Flavouring | 1.5 mg |  |
| Citric Acid | 0.1 mg |  |
| Purified Water | qs | 1 ml |

Dissolve the parabens in a small portion of the water that has been heated to approximately 90° C. Add the paraben solution to a large portion of the remaining water with mixing. Add and dissolve the other components. Bring the formulation to final volume and mix until homogenous. Fill the formulation into a containing, such as a unit dose cup or a bottle for multiple-dose use, to provide 5 mg/ml of the compound of Example 2 free base.

Example G

TRANSDERMAL SYSTEM

| Compound of Example 2 (dihydrochloride) | 5% (of compound of formula (I)) |
|---|---|
| Silicone fluid | 90% |
| Colloidal silicone dioxide | 5% |

The silicone fluid and drug are mixed together and the colloidal silicone dioxide is added to increase the viscosity. The material is then dosed into a subsequently heat sealed polymeric laminate comprised of the following: polyester release liner, skin contact adhesive composed of silicone or acrylic polymers, a control membrane which is a polyolefin (e.g. polyethylene or polyvinyl acetate) or polyurethane, and an impermeable backing membrane of a polyester multilaminate.

Example H

LYOPHILIZED PRODUCT

| Compound of Example 2 (dihydrochloride) |  | 6.0 mg |
|---|---|---|
| Mannitol |  | 50.0 mg |
| Acetate buffer |  | 8.2 mg |
| Water for injection | qs | 1 ml |

Dissolve components in a portion of the water for injection. Make formulation up to final volume and mix until homogenous. Filter formulation through a sterilising filter and fill into glass vials. Lyophilize and seal vials. Reconstitute with appropriate solvent prior to use.

Example I

HARD GELATIN CAPSULE

| Compound of Example 2 (dihydrochloride) |  | 12.00 mg |
|---|---|---|
| Lactose |  | 80.00 mg |
| Magnesium Stearate |  | 0.75 mg |
| Avicel pH 102 | qs | 150.00 mg |

The compound of Example 2 (dihydrochloride) is passed through a 30 mesh sieve and blended with lactose, Avicel pH 102 and magnesium stearate. The resultant mix is encapsulated into hard gelatin capsules using a suitable capsule machine, to provide 10 mg/capsule of the compound of Example 2 free base.

Capsules of other strengths can be similarly made to provide 0.5, 2 and 5 mg/capsule of compound of Example 2 free base.

Biological Data

As mentioned hereinbefore, compounds of the invention have been shown to inhibit radiation-induced emesis in the ferret using the test as described hereinbefore. More specifically the compound of Example 2, (2-Methoxy-5-tetrazol-1-yl-benzyl)-([2S,3S]-2-phenyl-piperidin-3-yl)-amine dihydrochloride, inhibited radiation-induced emesis in the ferret, administering the compound 1.5 hours prior to irradiation, at a dose of 0.1 mg/kg s.c. The compound of Example 7, [2-Methoxy-5-(5-trifuoromethyl-tetrazol-1-yl)-benzyl]-([2S,3S]-2-phenyl-piperidin-3-yl)-amine dihydrochloride, inhibited radiation-induced emesis in the ferret, administering the compound 1.5 hours prior to irradiation, at a dose of 0.03 mg/kg s.c.

No apparent adverse or toxic effects were observed during the above in vivo tests due to the administration of the compounds of the invention.

What is claimed is:

1. A compound of formula (I)

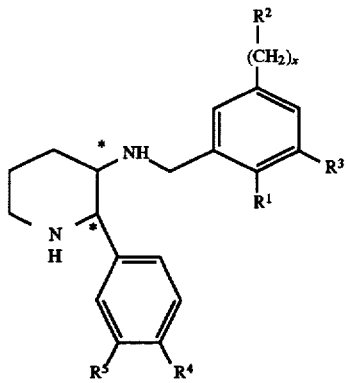

wherein $R^1$ is a $C_{1-4}$alkoxy group;
$R^2$ is

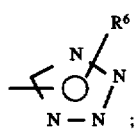

$R^3$ is a hydrogen or halogen atom;
$R^4$ and $R^5$ may each independently represent a hydrogen or halogen atom, or a $C_{1-4}$alkyl, $C_{1-4}$alkoxy or trifluoromethyl group;
$R^6$ is a hydrogen atom, a $C_{1-4}$alkyl, $(CH_2)_m$cyclopropyl, $-S(O)_nC_{1-4}$alkyl, phenyl, $NR^7R^8$, $CH_2C(O)CF_3$ or trifluoromethyl group;
$R^7$ and $R^8$ may each independently represent a hydrogen atom, or a $C_{1-4}$alkyl or acyl group;
x represents zero or 1;
n represents zero, 1 or 2;
m represents zero or 1;
or a pharmaceutically acceptable salt or solvate thereof.

2. A compound according to claim 1 wherein $R^1$ is a $C_{1-4}$alkoxy group, $R^2$ is

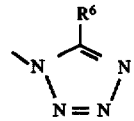

where $R^6$ is a hydrogen atom, a $C_{1-4}$alkyl, cyclopropyl or trifluoromethyl group, x is zero and $R^3$, $R^4$ and $R^5$ are each hydrogen atoms.

3. A compound according to claim 1 wherein $R^1$ is a methoxy group.

4. A compound according to claim 1 wherein $R^2$ is

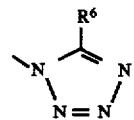

5. A compound according to claim 1 wherein $R^3$ is hydrogen.

6. A compound according to claim 1 wherein $R^4$ and $R^5$ are each hydrogen atoms.

7. A compound according to claim 1 wherein $R^6$ is hydrogen, a $C_{1-4}$alkyl or trifluoromethyl group.

8. A compound according to claim 1 wherein x is zero.

9. The compound which is (2-Methoxy-5-tetrazol-1-yl-benzyl)-(2S-phenyl-piperidin-3S-yl)-amine or a pharmaceutically acceptable salt or solvate thereof.

10. The compound which is [2-Methoxy-5-(5-trifluoromethyl-tetrazol-1-yl)-benzyl]-(2S-phenyl-piperidin-3S-yl)-amine or a pharmaceutically acceptable salt or solvate thereof.

11. A compound according to claim 9 in the form of its dihydrochloride salt.

12. A compound according to claim 1 for use in therapy.

13. A pharmaceutical composition comprising a compound according to claim 1 or a pharmaceutically acceptable salt or solvate thereof, together with a pharmaceutically acceptable carrier.

14. A method for the treatment of a condition mediated by tachykinins, including substance P and other neurokinins, in a mammal comprising administration of an effective amount of a compound according to claim 1 or a pharmaceutically acceptable salt or solvate thereof.

15. A process for preparing a compound of formula (I) as defined in claim 1, or a pharmaceutically acceptable salt or solvate thereof which comprises:

(A) reacting a compound of formula (II)

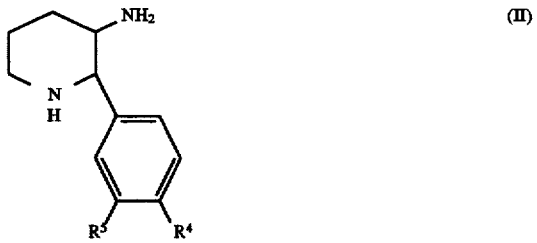

with a compound of formula (III)

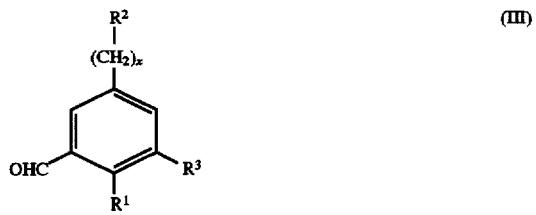

followed by reduction: or (B), a process for preparing a compound of formula (I) where $R^2$ is a group (A) as defined hereinbefore, x is zero and $R^6$ is $-NH_2$ which comprises reacting a compound of formula (XXIII)

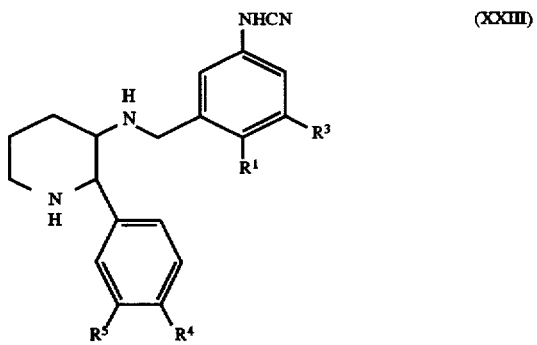

with ammonium chloride and sodium azide: or (C) reducing a compound of formula (XXIV)

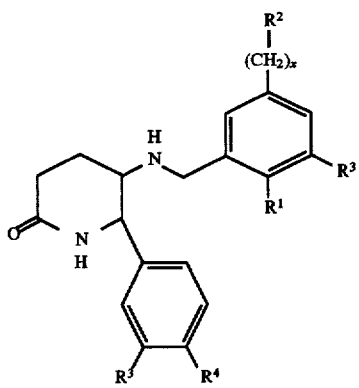
(XXIV)

16. A compound according to claim 10 in the form of its dihydrochloride salt.

17. A pharmaceutical composition comprising a compound of formula (I) as defined in claim 1 in combination with a 5HT$_3$ antagonist.

18. A pharmaceutical composition according to claim 17 wherein the 5HT$_3$ antagonist is selected from ondansetron, granisetron or metoclopramide.

19. A method of treatment according to claim 14 wherein the condition is emesis.

20. A method of treatment according to claim 14 wherein the condition is pain.

* * * * *